United States Patent
Villalba Gonzalez et al.

(10) Patent No.: US 10,969,391 B2
(45) Date of Patent: Apr. 6, 2021

(54) METHODS FOR DIAGNOSING HEMATOLOGICAL CANCERS

(71) Applicants: INSERM (INSTITUT NATIONAL DE LA SANTÉ ET DE LA RECHERCHE MÉDICALE), Paris (FR); CENTRE HOSPITALIER UNIVERSITAIRE DE MONTPELLIER, Montpellier (FR); UNIVERSITE DE MONTPELLIER, Montpellier (FR)

(72) Inventors: Martin Villalba Gonzalez, Montpellier (FR); Ewelina Krzywinska, Montpellier (FR)

(73) Assignees: INSERM (INSTITUT NATIONAL DE LA SANTÉ ET DE LA RECHERCHE MÉDICALE), Paris (FR); CENTRE HOSPITALIER UNIVERSITAIRE DE MONTPELLIER, Montpellier (FR); UNIVERSITE DE MONTPELLIER, Montpellier (FR)

( * ) Notice: Subject to any disclaimer, the term of this patent is extended or adjusted under 35 U.S.C. 154(b) by 151 days.

(21) Appl. No.: 15/324,652

(22) PCT Filed: Jul. 10, 2015

(86) PCT No.: PCT/EP2015/065797
§ 371 (c)(1),
(2) Date: Jan. 6, 2017

(87) PCT Pub. No.: WO2016/005548
PCT Pub. Date: Jan. 14, 2016

(65) Prior Publication Data
US 2018/0052166 A1 Feb. 22, 2018

(30) Foreign Application Priority Data

Jul. 11, 2014 (EP) .................................. 14306134
Jan. 7, 2015 (EP) .................................. 15305011

(51) Int. Cl.
*G01N 33/574* (2006.01)

(52) U.S. Cl.
CPC . *G01N 33/57426* (2013.01); *G01N 33/57484* (2013.01); *G01N 2333/70589* (2013.01); *G01N 2800/52* (2013.01)

(58) Field of Classification Search
CPC ....... G01N 33/57426; G01N 33/57484; G01N 2333/70589
See application file for complete search history.

(56) References Cited

PUBLICATIONS

Caligiuri, M.A., "Human Natural Killer Cells," Blood 112(3):461-469, Aug. 2008.
Fu, X., et al., "Human Natural Killer Cells Expressing the Memory-Associated Marker CD45RO From Tuberculous Pleurisy Respond More Strongly and Rapidly Than CD45RONatural Killer Cells Following Stimulation With Interleukin-12," Immunology 134(1):41-49, Sep. 2011.
International Search Report and Written Opinion dated Aug. 14, 2015, issued in corresponding International Application No. PCT/EP2015/065797, filed Jul. 10, 2015, 11 pages.
Krzywinska, E., "Study of the Cytotoxicity of Activated NK Cells on Specific Tumour Cells From Patients With Different Haematopoietic Malignancies," ImmunoTools IT-Box-139 Award 2013, May 17, 2013, <http://www.immunotools.de/html/award/EwelinaKrzywinska.pdf> [retrieved Dec. 16, 2016], 2 pages.
Lima, M., et al., "The 'Ex Vivo' Patterns of CD2/CD7, CD57/CD11c, CD38/CD11b, CD45RA/CD45RO, and CD11a/HLA-DR Expression Identify Acute/Early and Chronic/Late NK-Cell Activation States," Blood Cells, Molecules, and Diseases 28(2):181-190, Mar.-Apr. 2002.
Olson, J.A., et al., "NK Cells Mediate Reduction of GVHD by Inhibiting Activated, Alloreactive T Cells While Retaining GVT Effects," Blood 115(21):4293-4301, May 2010.
Romee, R., et al., "Cytokine Activation Induces Human Memory-Like NK Cells," Blood 120(24):4751-4760, Dec. 2012.

*Primary Examiner* — Mark Halvorson
(74) *Attorney, Agent, or Firm* — Christensen O'Connor Johnson Kindness PLLC

(57) ABSTRACT

The present invention relates to methods for diagnosing hematological cancers. In particular, the present invention relates to a method for diagnosing a hematological cancer in a patient comprising i) detecting the presence of CD45RARO NK cells in a sample obtained from the patient and ii) and concluding that the patient suffers from a hematological cancer when the presence of CD45RARO NK cells is detected in the sample and the presence of at least one phenotypic marker indicates the nature of the haematological cancer.

9 Claims, 23 Drawing Sheets

METHODS FOR DIAGNOSING HEMATOLOGICAL CANCERS

FIELD OF THE INVENTION

Figure 1A:
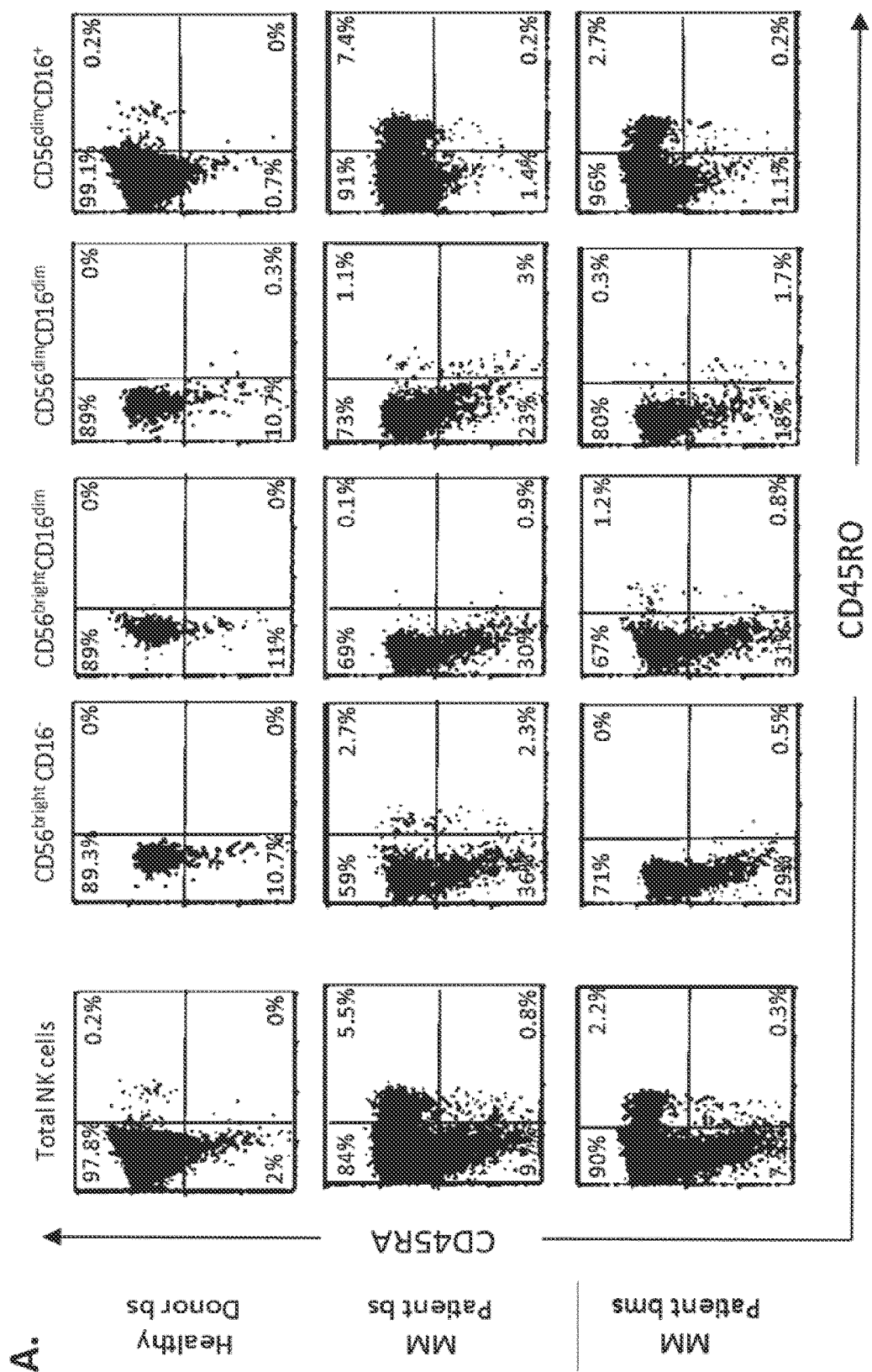

The present invention relates to methods for diagnosing hematological cancers.

BACKGROUND OF THE INVENTION

Natural Killer (NK) cells are members of the lymphocyte lineage and belong to the innate immune system. They show natural cytotoxicity and produce cytokines[1,2]. The majority of human NK cells in peripheral blood are $CD3^-CD56^{dim}$ cells while the minority shows a $CD3^-CD56^{bright}$ phenotype. The last population shines at cytokine production whereas $CD56^{dim}$ cells show mainly cytotoxic activity[3]. In contrast $CD3^-CD56^{bright}$ cells are majority in lymph nodes and tonsils. In vitro evidence indicates that $CD56^{bright}$ cells are precursors of $CD56^{dim}$ cells, which can also be the case in vivo[4]. In addition, CD16 expression suggests that NK cell development follows this pathway: $CD56^{bright}CD16^- \rightarrow CD56^{bright}CD16^{dim} \rightarrow CD56^{dim}CD16^{dim} \rightarrow CD56^{dim}CD16^+$. Additional markers can identify additional subsets in these populations[5,6]. In contrast, identification of activated NK cells in vivo has been probed more difficult. CD69 expression increases after NK cell stimulation and is considered a bona fide marker of activation including in humans[7], although its long-lasting expression is unknown. In mice, the stable expression of CD69 after long-term stimulus is disputed: after murine CMV infection CD69 expression is transient[8] whereas after IL-15 treatment is stable[9].

NK cells are activated after encountering their targets, which are mostly cells with altered expression of the major histocompatibility complex-I (MHC-I), which include transformed or virus-infected cells, which down regulate MHC-I expression to evade recognition by cytotoxic T lymphocytes (CTL). The "missing self" hypothesis proposes that NK cells distinguish target cells from other healthy "self" cells based on MHC-I expression. NK cell activation depends on a complex signaling mechanism mediated by both activating and inhibitory receptors. The main NK cell inhibitory receptors recognize MHC-I, called HLA in humans, complexes and include NKG2A, which recognizes HLA-E, and Killer-cell Immunoglobulin-like Receptors (KIRs), which recognize the self classical class I molecules HLA-A, -B and -C. Activating NK cell receptors perceive stress and/or non-self ligands on cells, i.e. the stress-induced ligands UL16-binding protein (ULBP) and MHC class I polypeptide-related sequence (MIC) are recognized by the activating receptor NKG2D[2].

NK cells recognize and eliminate blood-borne cancer cells. However, these tumor cells found different mechanism for immune escape[10,11] and a significant number of these patients show limited long-term survival. Some options to treat these patients include new chemicals that can be associated to immunotherapy[12]. The first clinical trial using an anti-KIR that can block KIR-mediated inhibition of NK cells has recently been published[7]. It shows absence of toxicity and favorably overall and relapse-free survival compared to reports in comparable patient populations of acute myeloid leukemia (AML). An interesting alternative to this therapy is using allogeneic NK cells because clinical-grade production has proven efficient[13], and NK cell-mediated therapy after hematopoietic cell transplantation seems safe[14-16]. However, NK cells are not a homogenous population, there are different subsets keeping different physiological activities. Moreover, different pattern of NK cell activation, e.g. cytokines vs targets cells, originates different transcriptional patterns[17]. It would be interesting to identify the populations with higher anti-tumor activity and select them for expansion and/or patient infusion.

Protein tyrosine phosphatases (PTPs) regulate cellular processes including differentiation, mitotic cycle, cell growth and oncogenic transformation[18]. CD45 is a PTP encoded by the PTPRC gene, which is specifically expressed in hematopoietic cells[19]. CD45 regulates receptor signaling by direct interaction with components of the receptor complexes or by dephosphorylating and activating various Src family kinases (SFK) i.e. Lck[20]. But it can inhibit cytokine receptor signaling by inhibiting JAK kinases[21] or by dephosphorylating the activating residues of Src[20]. CD45 activity is critical for an efficient immune response, because its deficiency results in a severe combined immunodeficiency (SCID) phenotype in both mice[22-24] and humans[25,26]. This could explain the high expression of this phosphatase and its complex regulation.

CD45 expression increases with cell maturation[27]. The CD45 family comprises several members derived from a single complex gene[27]. Naive T lymphocytes are usually positive for the long CD45RA isoform. Activated and memory T cells express CD45RO, the shortest CD45 isoform by activation-induced alternative splicing of CD45 pre-mRNA[27-30]. It has been proposed that CD45RO expression also identifies memory NK cells[31].

Most studies in CD45 function have been developed in T cells. Much less is known about its function on NK cells, although it is commonly accepted that CD45 positively regulates the activation of these cells through its ability to dephosphorylate the inhibitory site of SFKs, leading to cytokine and chemokine production. However, in vitro cytotoxicity is only slightly impaired in NK cells derived from CD45-deficient mice[32-34]. Moreover, in contrast to T and B cells, CD45-deficient NK cells show increased basal phosphorylation of multiple phosphoproteins suggesting that CD45 dephosphorylates multiple substrates in NK cells, including the activating tyrosine residue of SFKs[34]. In vivo studies show that CD45-deficient NK cells do not protect mice from cytomegalovirus infection due to impaired function of all immunoreceptor tyrosine-based activation motif (ITAM)-dependent NK cell functions, including degranulation[35]. Most of the results cited above were obtained in mouse models and could not reflect the human sketch. Hence, the role of CD45 in human NK cells is an open issue, which could depend on the type and strength of the activation.

SUMMARY OF THE INVENTION

The present invention relates to methods for diagnosing hematological cancers. In particular, the present invention is defined by the claims.

DETAILED DESCRIPTION OF THE INVENTION

The NK cell lymphocyte lineage plays an important role in the antitumor immune response. The full mature $CD56^{dim}CD16^+$ population show the higher cytolytic activity reliable to this function, but little is known about the cells responsible of it. One of the main markers of the lymphocyte lineage is the phosphatase CD45 that is present in two main isoforms in T lymphocytes with the resting T cells expressing the large CD45RA isoform and the effector/memory T cells expressing the short CD45RO isoform. Here the inventors show that NK cells from healthy donors mostly are CD45RA$^{high}$RO$^-$ whereas 3% of them are CD45RA$^{dim}$RO$^-$, which are 10 times more abundant in HSC allografted patients and mainly corresponds to immature cells. Hematological cancer patients also show a 5 times increase on this population that is also found in their full mature NK cell compartment. But these cells do not show high degranulating activity. Some NK cells from these patients gain CD45RO expression generating a minority of CD45RA$^{dim}$RO cells, which belongs to the CD56$^{dim}$CD16$^{dim}$ compartment, and a majority of cells that do not lost CD45RA expression: CD45 RARO cells. This population belongs to the full mature compartment and represents the antitumor NK cells. This is based on the facts that CD45 RARO cells: i) have recently degranulated; ii) show high size (FS) and granularity (SS); iii) show high metabolism (CD71$^+$); and iv) are proliferating (Ki-67$^-$). The definitive evidence that these cells are performing antitumor function is giving by the fact that they have performed trogocytosis in vivo in human leukemia patients. The presence of CD45 RARO NK cells in blood or bone marrow identifies blood-borne cancer patients and could be used as a diagnostic tool.

Accordingly, the present invention relates to a method for diagnosing a haematological cancer in a patient comprising i) detecting the presence of CD45 RARO NK cells in a sample obtained from the patient and ii) and concluding that the patient suffers from a haematological cancer when the presence of CD45 RARO NK cells is detected in the sample.

As used herein, the term "haematological cancer" or "blood-borne cancer" has its general meaning in the art and refers to cancers that typically arise from blood cells or bone marrow cells.

In some embodiments, the method of the present invention is particularly suitable for diagnosing a haematological cancer selected from the group consisting of leukemia, lymphoma and myeloma.

In some embodiments, haematological cancer such as lymphoma is a mature (peripheral) B-cell neoplasm. In specific embodiments, the mature B-cell neoplasm is selected from the group consisting of B-cell chronic lymphocytic leukemia/small lymphocytic lymphoma; B-cell prolymphocytic leukemia; Lymphoplasmacytic lymphoma; Marginal zone lymphoma, such as Splenic marginal zone B-cell lymphoma (+/−villous lymphocytes), Nodal marginal zone lymphoma (+/−monocytoid B-cells), and Extranodal marginal zone B-cell lymphoma of mucosa-associated lymphoid tissue (MALT) type; Hairy cell leukemia; Plasma cell myeloma/plasmacytoma; Follicular lymphoma, follicle center; Mantle cell lymphoma; Diffuse large cell B-cell lymphoma (including Mediastinal large B-cell lymphoma, Intravascular large B-cell lymphoma, and Primary effusion lymphoma); and Burkitt's lymphoma/Burkitt's cell leukemia.

In some embodiments, haematological cancer such as lymphoma is selected from the group consisting of multiple myeloma (MM) and non Hodgkin's lymphoma (NHL), mantle cell lymphoma (MCL), follicular lymphoma, Waldenstrom's macroglobulinemia (WM) or B-cell lymphoma and diffuse large B-cell lymphoma (DLBCL). In some embodiments, Non-Hodgkin's Lymphoma (NHL) falls into one of two categories, aggressive NHL or indolent NHL. Aggressive NHL is fast growing and may lead to a subject's death relatively quickly. Untreated survival may be measured in months or even weeks. Examples of aggressive NHL includes B-cell neoplasms, diffuse large B-cell lymphoma, T/NK cell neoplasms, anaplastic large cell lymphoma, peripheral T-cell lymphomas, precursor B-lymphoblastic leukemia/lymphoma, precursor T-lymphoblastic leukemia/lymphoma, Burkitt's lymphoma, Adult T-cell lymphoma/leukemia (HTLV1+), primary CNS lymphoma, mantle cell lymphoma, polymorphic post-transplantation lymphoproliferative disorder (PTLD), AIDS-related lymphoma, true histiocytic lymphoma, and blastic NK-cell lymphoma. The most common type of aggressive NHL is diffuse large cell lymphoma. Indolent NHL is slow growing and does not display obvious symptoms for most subjects until the disease has progressed to an advanced stage. Untreated survival of subjects with indolent NHL may be measured in years. Nonlimiting examples include follicular lymphoma, small lymphocytic lymphoma, marginal zone lymphoma (such as extranodal marginal zone lymphoma (also called mucosa associated lymphoid tissue—MALT lymphoma), nodal marginal zone B-cell lymphoma (monocytoid B-cell lymphoma), splenic marginal zone lymphoma), and lymphoplasmacytic lymphoma (Waldenstrom's macroglobulinemialn some cases, histologic transformation may occur, e.g., indolent NHL in subjects may convert to aggressive NHL.

In some embodiments, haematological cancer such as leukemia is selected from the group consisting of acute lymphocytic leukemia (ALL), acute myeloid leukemia (AML), chronic lymphocytic leukemia (CLL), and small lymphocytic lymphoma (SLL). Acute lymphocytic leukemia is also known as acute lymphoblastic leukemia and may be used interchangeably herein. Both terms describe a type of cancer that starts from the white blood cells, lymphocytes, in the bone marrow.

In some embodiments, the sample is a blood sample or is a bone marrow sample.

As used herein, the term "blood sample" has its general meaning in the art ant typically refers to a whole blood sample obtained from the patient. In some embodiments, the blood sample is a PBMC sample. The term "PBMC" or "peripheral blood mononuclear cells" or "unfractionated PBMC", as used herein, refers to whole PBMC, i.e. to a population of white blood cells having a round nucleus, which has not been enriched for a given sub-population. Typically, the PBMC sample may have been subjected to a selection step to contain non-adherent PBMC (which contain T cells, B cells, natural killer (NK) cells, NK T cells and DC precursors). A PBMC sample according to the invention therefore contains lymphocytes (B cells, T cells, NK cells, NKT cells). Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis buffer, which will preferentially lyse red blood cells. Such procedures are known to the expert in the art. The NK cells can be prepared by Percoll density gradients, by negative depletion methods or by FACS sorting methods. These cells can also be isolated by column immunoadsorption using an avidine-biotin system or by immunoselection using microbeads grafted with antibodies. It is also possible to use combinations of these different techniques, optionally combined with plastic adherence methods.

As used herein, the term "bone marrow sample" has its general meaning in the art. The term bone marrow sample emcompasses "bone marrow aspirates," which refer to material pulled out the bone marrow cavity by suction, which includes, but is not limited to, bone marrow aspiration and bone marrow biopsy.

As used herein, the term "NK cell" has its general meaning in the art and refers to natural killer (NK) cell. One skilled in the art can easily identify NK cells by determining for instance the expression of specific phenotypic marker (e.g. CD56) and the ability to express different kind of cytokines or the ability to induce cytotoxicity.

In some embodiments, the method of the present invention comprises a step consisting of isolating the population of NK cells in the sample (e.g. PBMC sample). Methods for isolating NK cells are well known in the art. NK cells are isolated by depletion of non-target cells (e.g. T cells, B cells, dendritic cells . . . ). Non target-cells are indirectly magnetically labeled with a cocktail of biotin-conjugated antibodies against lineage-specific antigens and a cocktail of Microbeads. The magnetically labeled non-target cells are depleted by retaining them within a MACS Column in the magnetic field of MACS Separator, while the unlabeled NK cells run through the column. The purity of the enriched NK cells can be evaluated by flow cytometry or fluorescence microscopy.

As used herein, the term "CD45 RARO NK cells" refers to the subset of NK cells expressing both markers CD45RA and CD45RO.

As used herein the term "CD45" has its general meaning in the art and refers to the protein tyrosine phosphatase (PTP) encoded by the PTPRC gene, which is specifically expressed in hematopoietic cells[19]. CD45 regulates receptor signalling by direct interaction with components of the receptor complexes or by activating and dephosphorylating various Src family kinases (SFK) i.e. Lck[20]. But it can inhibit cytokine receptor signalling by inhibiting JAK kinases or by dephosphorylating the activating residues of Src[20]. Typically it is possible to distinguish two isoforms of CD45: CD45RA and CD45RO. The term "CD45RA" the CD45 isoform in which exon 4 of the CD45 gene is not expressed. The term "CD45RO" refers to the CD45 iso form in which exons 4, 5, and 6 of the CD45 gene are not expressed.

Typically the presence of CD45 RARO NK cells in the blood sample of the patient consists in detecting the presence and/or absence of some specific cell surface markers. Standard methods for detecting the expression of specific surface markers at cell surface (e.g. NK cell surface) are well known in the art. Typically, the step consisting of detecting the presence of CD45 RARO NK cells involves use of a set of binding partners that are suitable for distinguishing NK cells from other cells and a set of binding partner comprising at least one differential binding partner directed specific for CD45RA and at least one differential binding partner directed specific for CD45RO.

As used herein, the term "binding partner directed specific for a surface marker" refers to any molecule (natural or not) that is able to bind said surface marker (e.g. CD4RA or CD45R0) with high affinity. Said binding partners include but are not limited to antibodies, aptamer, and peptides. The binding partners may be antibodies that may be polyclonal or monoclonal, preferably monoclonal (e.g Kit Milteny CD45RA & CD45RO antibodies). In some embodiments, the binding partners may be a set of aptamers.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies of the invention or a fragment thereof can be prepared and isolated using any technique that provides for the production of antibody molecules by continuous cell lines in culture. Techniques for production and isolation include but are not limited to the hybridoma technique originally; the human B-cell hybridoma technique; and the EBV-hybridoma technique.

In some embodiments, the binding partners may be aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA or RNA. In this library, each member is a linear oligomer, eventually chemically modified, of a unique sequence. Peptide aptamers consist of conformationally constrained antibody variable regions displayed by a platform protein, such as *E. coli* Thioredoxin A that are selected from combinatorial libraries by two hybrid methods.

The binding partners of the invention such as antibodies or aptamers are typically labelled with a detectable molecule or substance, such as preferentially a fluorescent molecule, or a radioactive molecule or any others labels known in the art. Labels are known in the art that generally provide (either directly or indirectly) a signal. As used herein, the term "labelled", with regard to the antibody or aptamer, is intended to encompass direct labelling of the antibody or aptamer by coupling (i.e., physically linking) a detectable substance, such as a fluorophore [e.g. fluorescein isothiocyanate (FITC) or phycoerythrin (PE) or Indocyanine (Cy5)]) or a radioactive agent to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as $I^{123}$, $I^{124}$, $In^{111}$, $R^{186}$. In some embodiments, the antibodies are already conjugated to a fluorophore (e.g. FITC-conjugated and/or PE-conjugated).

The aforementioned assays typically involve the binding of the binding partners (ie. antibodies or aptamers) to a solid support. The solid surface could a microtitration plate coated with the binding partner. After incubation of the NK cell sample, NK cells specifically bound to the binding partner may be detected with an antibody to a common NK cell marker Alternatively, the solid surfaces may be beads, such as activated beads, magnetically responsive beads. Beads may be made of different materials, including but not limited to glass, plastic, polystyrene, and acrylic. In addition, the beads are preferably fluorescently labelled. In a preferred embodiment, fluorescent beads are those contained in TruCount™ tubes, available from Becton Dickinson Biosciences, (San Jose, Calif.).

According to the invention, methods of flow cytometry are preferred methods for detecting CD45 RARO NK cells. Said methods are well known in the art. For example, fluorescence activated cell sorting (FACS) may be therefore used. Typically, a FACS method such as described in Example here below is used.

In some embodiments, the method of the present invention further comprises the steps of detecting the presence of at least one phenotypic marker on said CD45 RARO NK cells wherein the presence of this at least one phenotypic marker indicates the nature of the haematological cancer.

In some embodiments, the method of the present invention comprises the step of detecting 1, 2, 3, 4, 5, 6, 7, 8, 9, 10, 11, 12, 13, 14, 15, 16, 17, 18, 19 or 20 phenotypic markers.

In some embodiments, the phenotypic marker is a CD molecule selected from the group consisting of CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15u, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD46, CD47R, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CD75, CD75s, CD77, CD79a, CD79b, CD80, CD81, CD82, CD83, CD84, CD85, CD86, CD87, CD88, CD89, CD90, CD91, CD92, CDw93, CD94, CD95, CD96, CD97, CD98, CD99, CD100, CD101, CD102, CD103, CD104, CD105, CD106, CD107a, CD107b, CD108, CD109, CD110, CD111, CD112, CDw113, CD114, CD115, CD116, CD117, CD118, CDw119, CD120a, CD120b, CD121a, CDw121b, CD122, CD123, CD124, CDw125, CD126, CD127, CDw128a, CDw128b, CD129, CD130, CD131, CD132, CD133, CD134, CD135, CDw136, CDw137, CD138, CD139, CD140a, CD140b, CD141, CD142, CD143, CD144, CDw145, CD146, CD147, CD148, CDw149, CD150, CD151, CD152, CD153, CD154, CD155, CD156a, CD156b, CDw156C, CD157, CD158, CD159a, CD159c, CD160, CD161, CD162, CD162R, CD163, CD164, CD165, CD166, CD167a, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CDw186, CD191, CD192, CD193, CD195, CD196, CD197, CDw198, CDw199, CDw197, CD200, CD201, CD202b, CD203c, CD204, CD205, CD206, CD207, CD208, CD209, CDw210, CD212, CD213a1, CD213a2, CDw217, CDw218a, CDw218b, CD220, CD221, CD222, CD223, CD224, CD225, CD226, CD227, CD228, CD229, CD230, CD231, CD232, CD233, CD234, CD235a, CD235b, CD235ab, CD236, CD236R, CD238, CD239, CD240CE, CD240D, CD240DCE, CD241, CD242, CD243, CD244, CD245, CD246, CD247, CD248, CD249, CD252 CD253, CD254, CD256, CD257, CD258, CD261, CD262, CD263, CD264, CD265, CD266, CD267, CD268, CD269, CD271, CD272, CD273, CD274, CD275, CD276, CD277, CD278, CD279, CD280, CD281, CD282, CD283, CD284, CD289, CD292, CDw293, CD294, CD295, CD296, CD297, CD298, CD299, CD300a, CD300c, CD300e, CD301, CD302, CD303, CD304, CD305, CD306, CD307, CD309, CD312, CD314, CD315, CD316, CD317, CD318, CD319, CD320, CD321, CD322, CD324, CDw325, CD326, CDw327, CDw328, CDw329, CD331, CD332, CD333, CD334, CD335, CD336, CD337, CDw338, and CD339.

Typically, the presence of at least one phenotypic marker selected from the group consisting of CD5, CD10, CD19, CD20, CD22, CD23, CD24, CD79a, CD103, Pax-5, kappa, lambda, CD200, cytoplasmic kappa, or cytoplasmic lambda indicates that the hematological cancer arising from a B cell. For example, Table A shows typical phenotypic markers of hematological cancer arising from B cells.

TABLE A typical phenotypic markers of hematological cancer arising from B cells

|       | CD19 | CD5 | CD23 | CD20 | CD22 | CD10 | CD11c | CD25 | CD103 |
|-------|------|-----|------|------|------|------|-------|------|-------|
| CLL   | +    | +   | +    | +    | +    |      |       | +    |       |
| B-PL  | +    |     |      | +    | +    |      |       |      |       |
| MCL   | +    | +   |      | +    | +    |      |       |      |       |
| MZLB  | +    |     |      | +    | +    |      | +     |      |       |
| sMZLB |      |     |      | +    | +    |      | +     |      | +     |
| FL    | +    |     |      | +    | +    | +    |       |      |       |

(CLL B-cell Chronic Lymphocytic Leukemia; B-PL B-cell prolymphocytic leukemia; MCL mantle cell lymphoma; MZLB Marginal zone lymphoma B-cell lymphoma; sMZLB Splenic marginal zone B-cell lymphoma; FL Follicular lymphoma)

Typically, the presence of at least one phenotypic marker selected from the group consisting of CD1, CD2, CD3, CD4, CD5, CD7, CD8, TCR α-β, TCR γ-δ, and CD3 indicated that the hematological cancer originates from a T cell.

Typically, the presence of at least one phenotypic marker selected from the group consisting of CD11b, CD13, CD14 (Mo2), CD14 (MY4), CD15, CD33, CD41, CD61 CD64, CD117, CD235a and myeloperoxidase indicates that the hematological cancer originates from a myeloid cell.

Typically detection of the phenotypic markers are performed according to the same protocols as done for CD45RA and CD45RO. Therefore a panel of binding partners can be used for determining the presence of the phenotypic marker and fluorescence activated cell sorting (FACS) is preferably used.

Once the patient is diagnosed as suffering from a haematological cancer, the physician can take the choice to administer the patient with the most accurate treatment. Typically, the treatment includes chemotherapy, radiotherapy, and immunotherapy.

Accordingly, the present invention also relates to a method for treating haematological cancer in a subject in need thereof comprising the steps of:

(i) identifying a subject having a haematological cancer by performing the method according to the method of this invention, (ii) treating said subject having a haematological cancer with a chemotherapeutic agent, a targeted cancer therapy, an immunotherapeutic agent or a radiotherapeutic agent.

In some embodiments, the patient once diagnosed as suffering from a haematological cancer is administered with a chemotherapeutic agent. The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the patient once diagnosed as suffering from a haematological cancer is administered with a targeted cancer therapy. Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the patient with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S. Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In certain embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the patient once diagnosed as suffering from a haematological cancer is administered with an immunotherapeutic agent. The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the patient with an amount of immune cells (T cells, NK, cells, dendritic cells, B cells . . . ).

Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors.

Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention.

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in patients undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin).

In addition to having specific or non-specific targets, immunotherapeutic agents can be active, i.e. stimulate the body's own immune response, or they can be passive, i.e. comprise immune system components that were generated external to the body.

Passive specific immunotherapy typically involves the use of one or more monoclonal antibodies that are specific for a particular antigen found on the surface of a cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins.

Monoclonal antibodies currently used as cancer immunotherapeutic agents that are suitable for inclusion in the combinations of the present invention include, but are not limited to, rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), and BL22. Other examples include anti-CTLA4 antibodies (e.g. Ipilimumab), anti-PD1 antibodies, anti-PDL1 antibodies, anti-TIMP3 antibodies, anti-LAG3 antibodies, anti-B7H3 antibodies, anti-B7H4 antibodies or anti-B7H6 antibodies. In some embodiments, antibodies include B cell depleting antibodies. Typical B cell depleting antibodies include but are not limited to anti-CD20 monoclonal antibodies [e.g. Rituximab (Roche), Ibritumomab tiuxetan (Bayer Schering), Tositumomab (GlaxoSmithKline), AME-133v (Applied Molecular Evolution), Ocrelizumab (Roche), Ofatumumab (HuMax-CD20, Gemnab), TRU-015 (Trubion) and IMMU-106 (Immunomedics)], an anti-CD22 antibody [e.g. Epratuzumab, Leonard et al., Clinical Cancer Research (Z004) 10: 53Z7-5334], anti-CD79a antibodies, anti-CD27 antibodies, or anti-CD19 antibodies (e.g. U.S. Pat. No. 7,109,304), anti-BAFF-R antibodies (e.g. Belimumab, GlaxoSmithKline), anti-APRIL antibodies (e.g. anti-human APRIL antibody, ProSci inc.), and anti-IL-6 antibodies [e.g. previously described by De Benedetti et al., J Immunol (2001) 166: 4334-4340 and by Suzuki et al., Europ J of Immunol (1992) 22 (8) 1989-1993, fully incorporated herein by reference].

The immunotherapeutic treatment may consist of allografting, in particular, allograft with hematopoietic stem cell HSC. The immunotherapeutic treatment may also consist in an adoptive immunotherapy as described by Nicholas P. Restifo, Mark E. Dudley and Steven A. Rosenberg "Adoptive immunotherapy for cancer: harnessing the T cell response, Nature Reviews Immunology, Volume 12, April 2012). In adoptive immunotherapy, the patient's circulating lymphocytes, NK cells, are isolated amplified in vitro and readministered to the patient. The activated lymphocytes or NK cells are most preferably be the patient's own cells that were earlier isolated from a blood or tumor sample and activated (or "expanded") in vitro.

In some embodiments, the patient once diagnosed as suffering from a haematological cancer is administered with a radiotherapeutic agent. The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

A further aspect of the present invention relates to a method for monitoring the efficiency of a treatment in a patient suffering from an haematological cancer comprising i) detecting the presence of CD45 RARO NK cells in a blood sample from the patient and ii) and concluding that the treatment of the patient is efficient when the presence of CD45 RARO NK cells is not detected in the blood sample.

Typically, the patient is administered with a treatment as described above.

The invention will be further illustrated by the following figures and examples. However, these examples and figures should not be interpreted in any way as limiting the scope of the present invention.

FIGURES

FIGS. 1A-1D. Patients with hematological malignancies and healthy donors have different NK cell subset profiles. 1A) PBMCs from blood samples (bs) of a healthy donor and of a patient with multiple myeloma (MM) or from bone marrow (bms) of the patient with MM were stained. The percentage of NK cells expressing the different CD45 iso forms is indicated in the panels. 1B) FS and SS value and maturation (CD56/CD16 expression) of the different NK cell subsets (based on the expression of CD45 isoforms) derived from a blood sample of a patient with MM. 1C) Percentage of these NK cell populations in healthy donors and in patients with hematological cancers. The bars show the mean±SD of at least four different individuals for each medical condition. HD, Healthy donor; MM, multiple myeloma; B-CLL, B-cell chronic lymphocytic leukemia; BCL, B-cell lymphoma; AML, acute myeloid leukemia; bs, blood samples; bms, bone marrow samples. 1D) Percentage of CD45RA, CD45 RARO, CD45RA$^{dim}$ and CD45RA$^{dim}$RO cells at the different stage of NK maturation (CD56/16 expression). Each point represents a donor. The mean±SD is also shown.

Figure 2A:
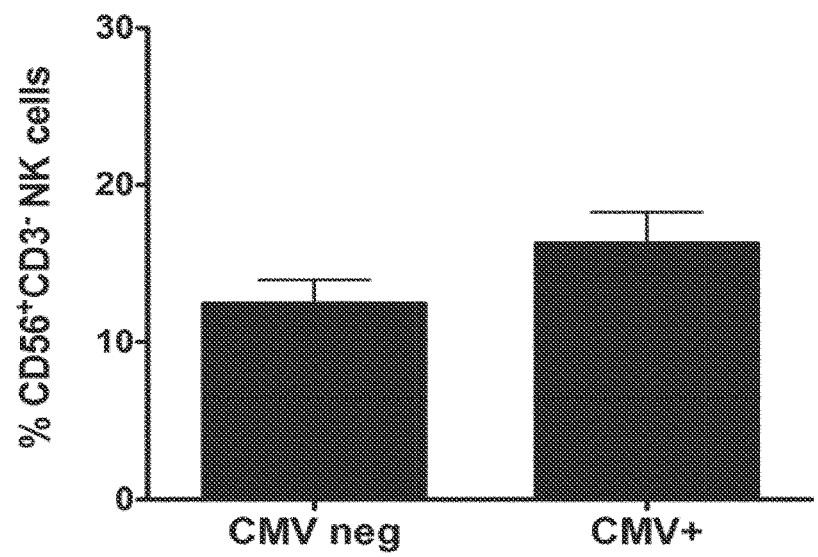
Figure 2B:
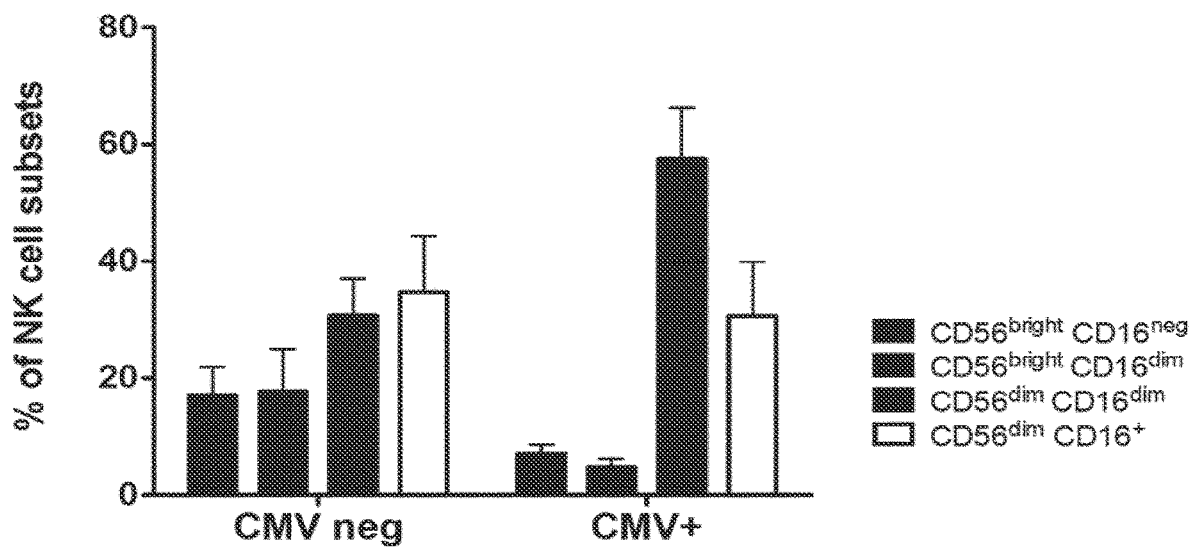
Figure 2C:
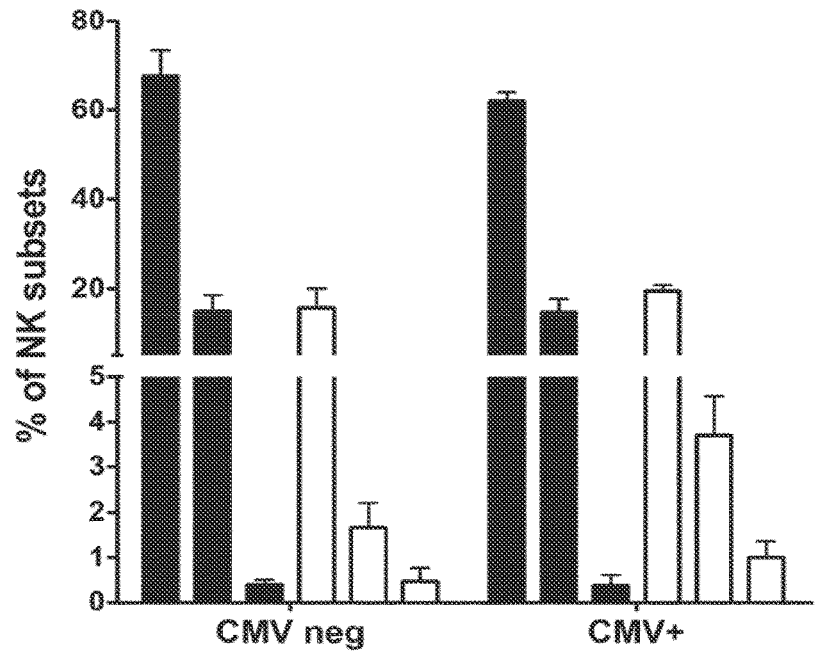

FIGS. 2A-2C. CMV+ patients and patients with hematological cancer have different NK cell subset profiles. 2A) PBMCs from patients with reactivation (CMV+) or not (CMVneg) of CMV infection following kidney transplantation were purified and the percentage of NK cells was calculated. 2B) The abundance (in percentage) of NK cells at different stages of maturation (CD56/CD16) was analyzed in the samples described in (2A). 2C) The percentage of each NK cell subsets (CD45 isoforms/CD69) is shown. In (2B) and (2C) bars represent the mean±SD of at least four individuals for each medical condition.

FIGS. 3A-3D. CD69, CD45RA and CD45RO identify different NK cell subsets. 3A) PBMCs from healthy donors (HD) and patients with different hematological malignancies were purified and the percentage of CD69$^+$ cells at different stages of NK cell maturation (CD56/CD16) was calculated. The mean±SD is also depicted. 3B) The percentage of NK cells that express or not CD45RA, CD45RO and CD69 in PBMCs from healthy donors (HD) and patients with different hematological malignancies is shown. Bars represent the mean±SD of at least four individuals for each medical condition. 3C-3D) Representative graphs showing the expression of CD45RO or CD45RA versus CD69 in NK cells from blood (bs) or bone marrow samples (bms) of patients with different blood-borne cancers. Bone marrow samples from healthy donors were not available for analysis.

FIGS. 4A-4E. CD45RO identifies different NK cell populations. PBMCs from healthy donors (HD) and patients with different hematological malignancies were purified. 4A) Number of CD107a$^+$ cells in each NK cell subset (CD45/CD69 expression) per million of NK cells. Bars represent the mean±SD of at least four individuals for each medical condition. B) Percentage of CD107a$^+$ NK cells in the six different subsets (CD45/CD69). 4C) Upper panels, Percentage of CD107a$^+$ cells in different NK cell subsets isolated from bone marrow samples (bms) of patients with MM (shown also the percentage in the corresponding blood sample, bs, for comparison) or AML. Bottom panels, Percentage of CD107a$^+$ cells in different NK cell subsets after exposure to target K562 tumor cells (in vitro cytotoxicity assay described in FIGS. 7A-7E). 4D-4E) Percentage of NK cells that express CD71 or Ki-67 in the six different NK cell subsets (CD45/CD69) from blood samples of healthy donors (HD) and patients with B-cell chronic lymphocytic leukemia (B-CLL) or B-cell lymphoma (BCL). Bars represent the mean±SD of at least four individuals for each medical condition.

Figure 5A:
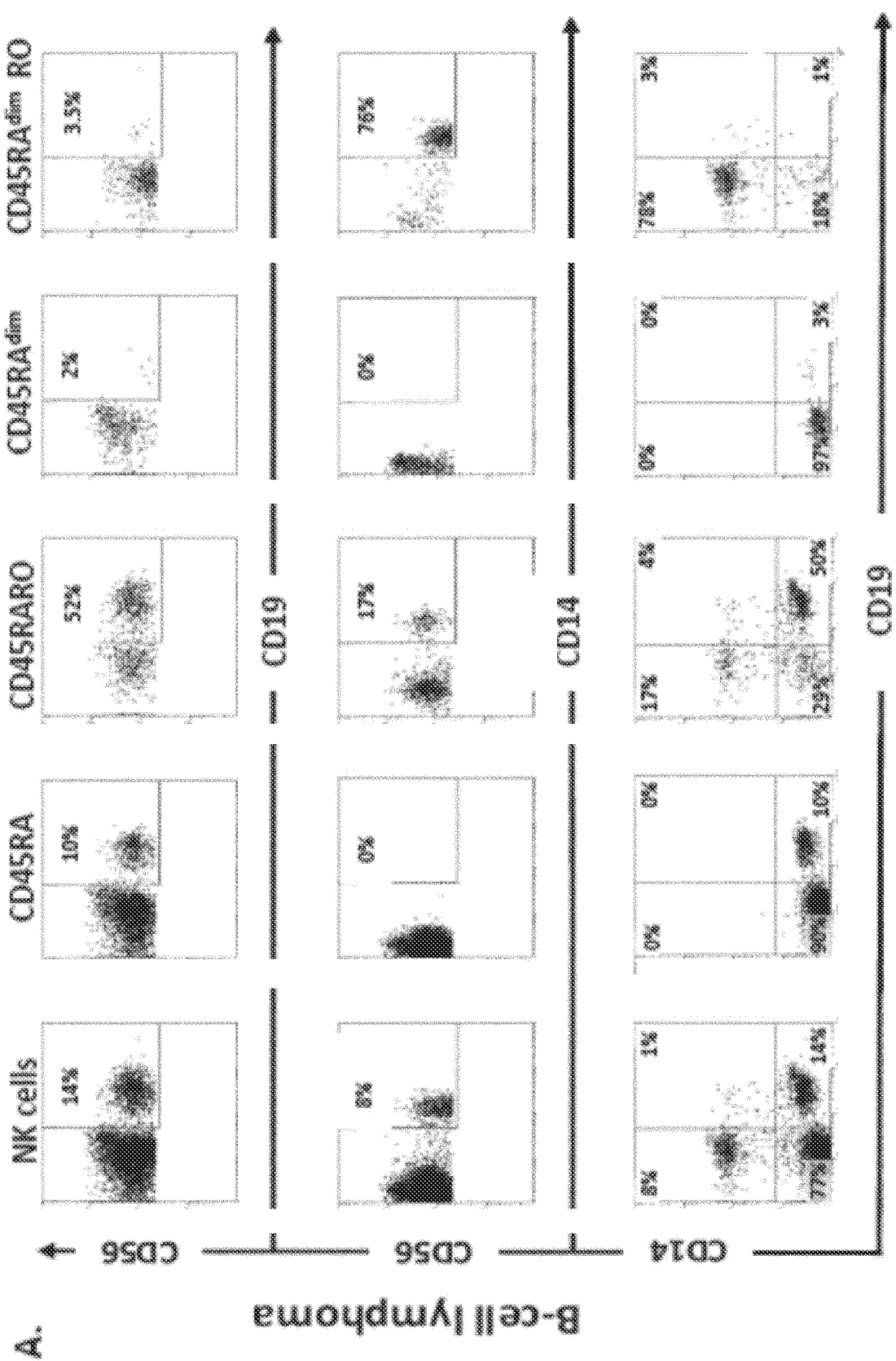
Figure 5B:
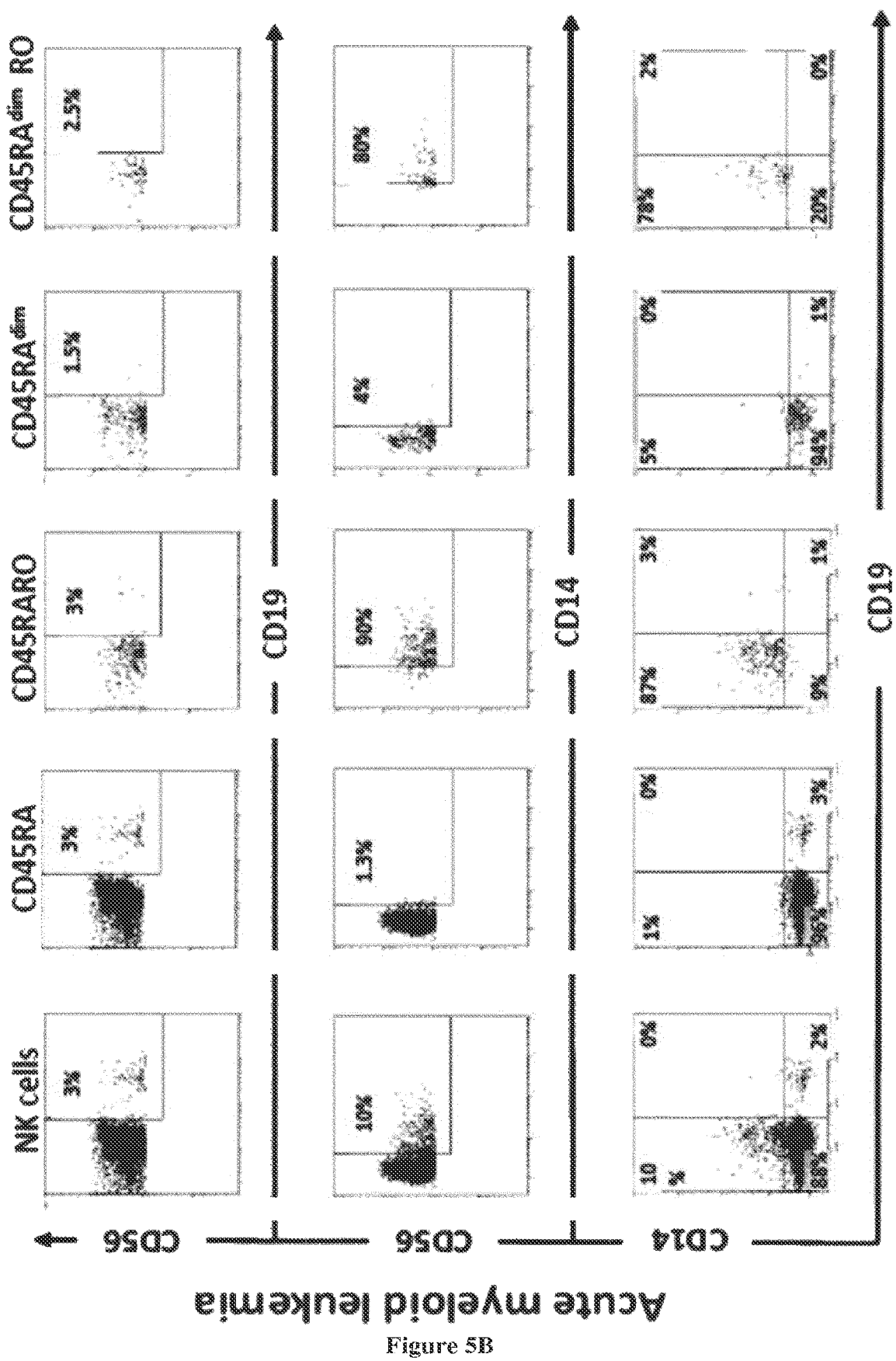

FIGS. 5A-5B. CD45 RARO cells have performed trogocytosis on tumor cells. PBMCs from patients with BCL (5A) or AML (5B) were purified and were stained with different antibodies. In this experiment, the NK cell population corresponded to CD56$^l$ NKP46$^l$ cells. The percentage of cells in each NK cell subset regarding CD45RA/RO is depicted in the graphics.

Figure 6A:
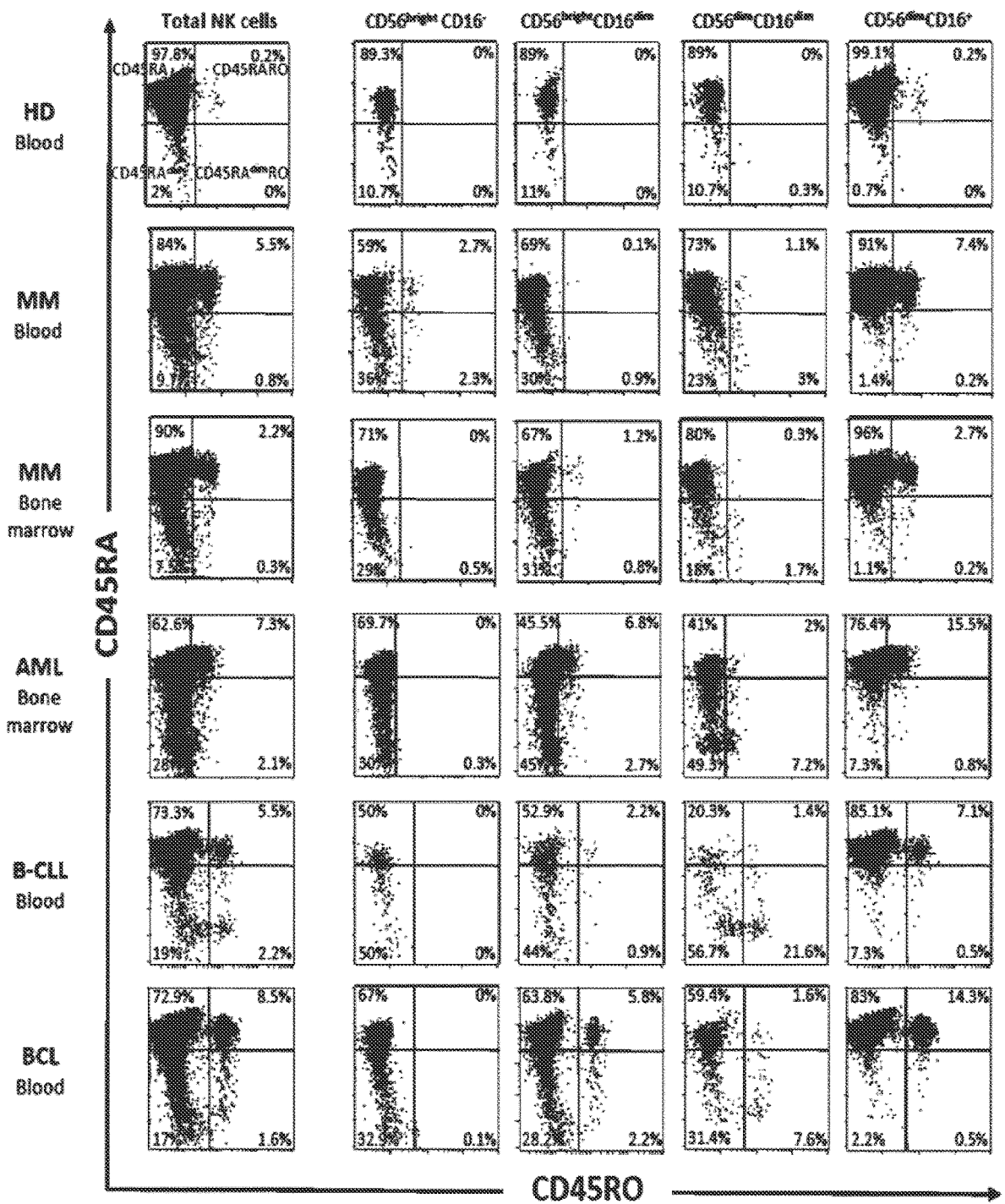
Figure 6B:
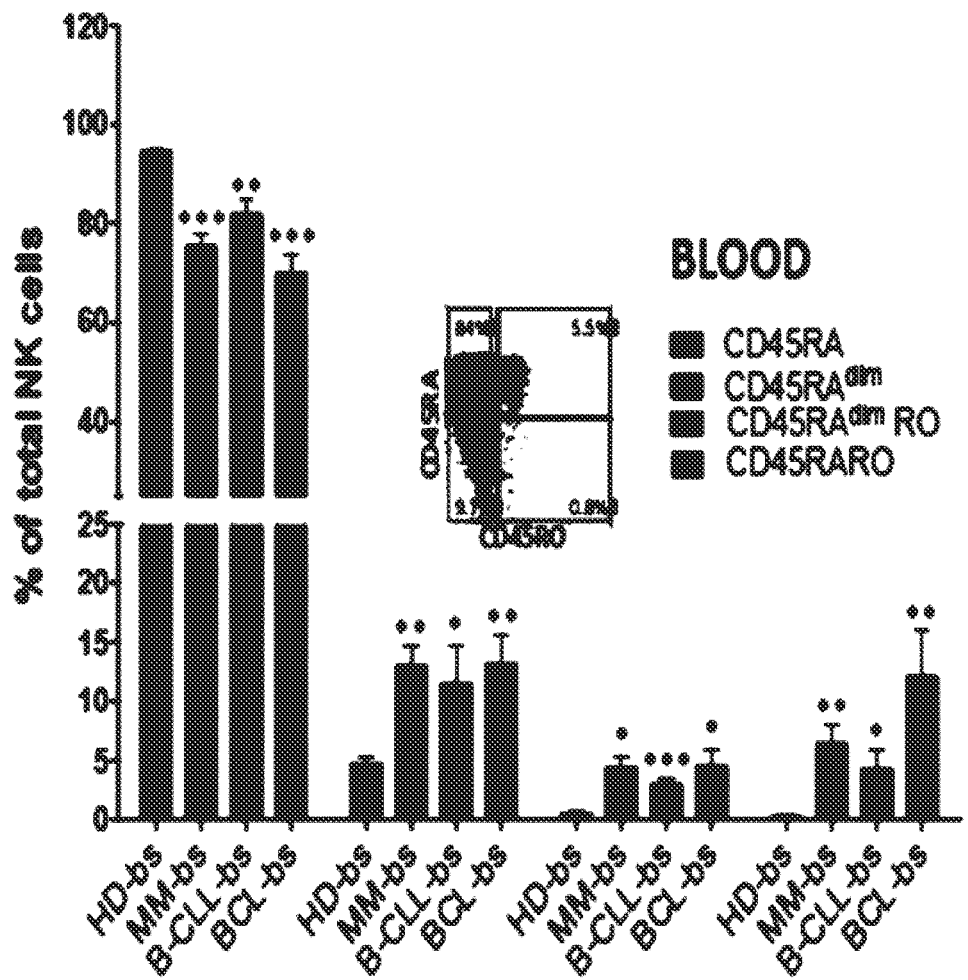
Figure 6B:
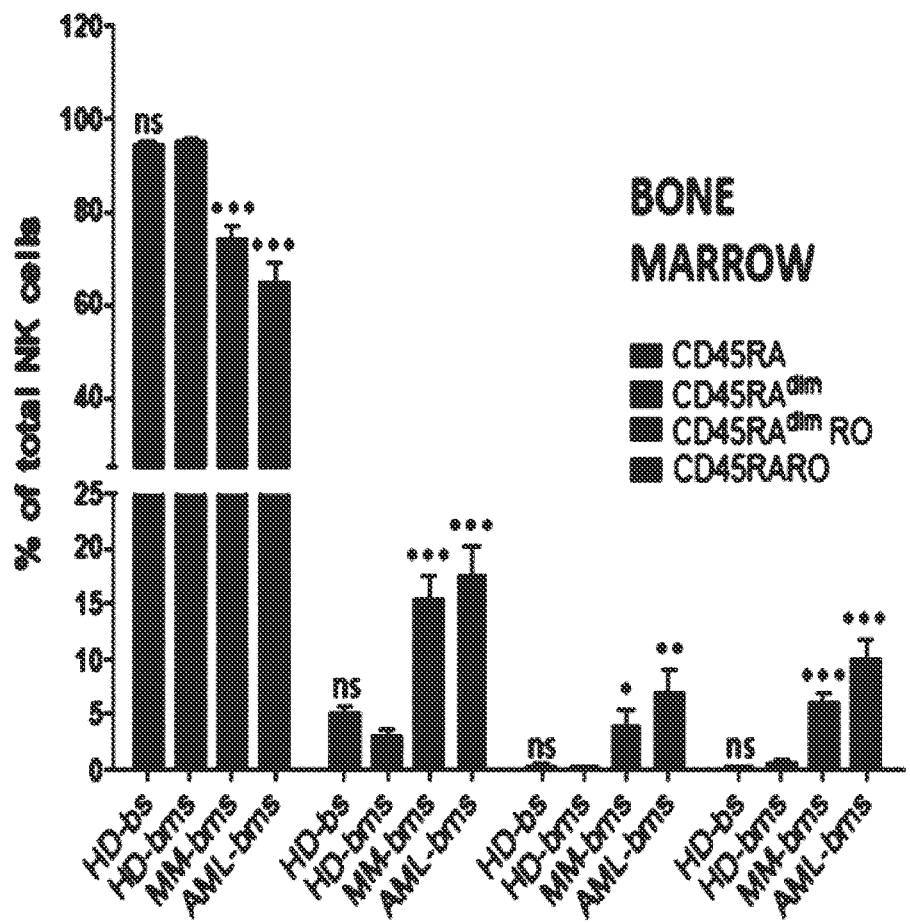

FIGS. 6A-6B. Patients with hematological malignancies and healthy donors have different NK cell subset profiles. 6A) PBMCs from blood samples (bs) of a healthy donor and of a patient with multiple myeloma (MM) or from bone marrow (bms) of the patient with MM or samples of patients with other hematological diseases were stained for FACS analysis with anti-CD19 (B cells), -CD3 (T cells, CD3$^+$ CD56$^-$) and -CD56 (NK cells, CD56$^+$CD3$^-$), to identify the different lymphocyte populations, and also with anti-CD16, to identify NK cell subsets at different stage of maturation, and with -CD45RA, and -CD45RO antibodies. The percentage of NK cells expressing the different CD45 isoforms is indicated in the panels. 6B) Percentage of different NK cell populations based on CD45RA and RO expression in healthy donors and in patients with hematological cancers. The populations correspond to the quadrants in FIG. 1A: upper left (CD45RA), bottom left (CD45RA$^{dim}$), upper right (CD45 RARO) and bottom right (CD45RA$^{dim}$RO). The bars show the mean±SD for each medical condition, student t-test compare to healthy donor blood (left panel) or bone marrow (right panel) samples: *p<0.01; p<0.001; *p<0.0001. HD, Healthy donor; MM, multiple myeloma; B-CLL, B-cell chronic lymphocytic leukemia; BCL, B-cell lymphoma; AML, acute myeloid leukemia; bs, blood samples; bms, bone marrow samples.

FIGS. 7A-7E. Functional characterization of CD45 RARO NK cells. 7A) FS and SS values of the different NK cell subsets (based on the expression of CD45 isoforms) derived from a blood sample of a patient with MM. 7B-7C) Expression of CD71 and Ki67 in the different NK cell subsets in a representative BCL patient. 7D-7E) Representative graphs showing the expression of CD45RO or CD45RA versus CD69 in NK cells from blood (bs) or bone marrow samples (bms) of patients with different blood-borne cancers.

Figures 8A, 8B:
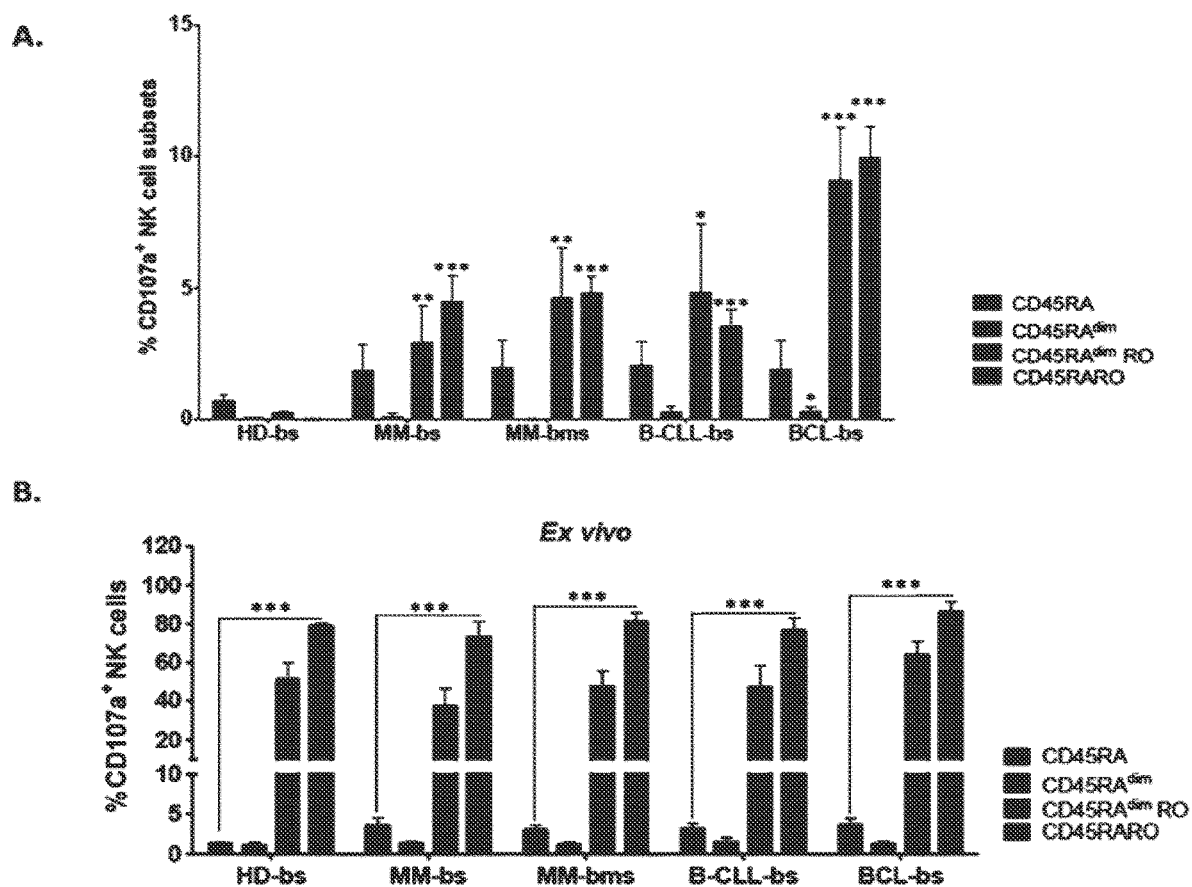
Figure 8C:
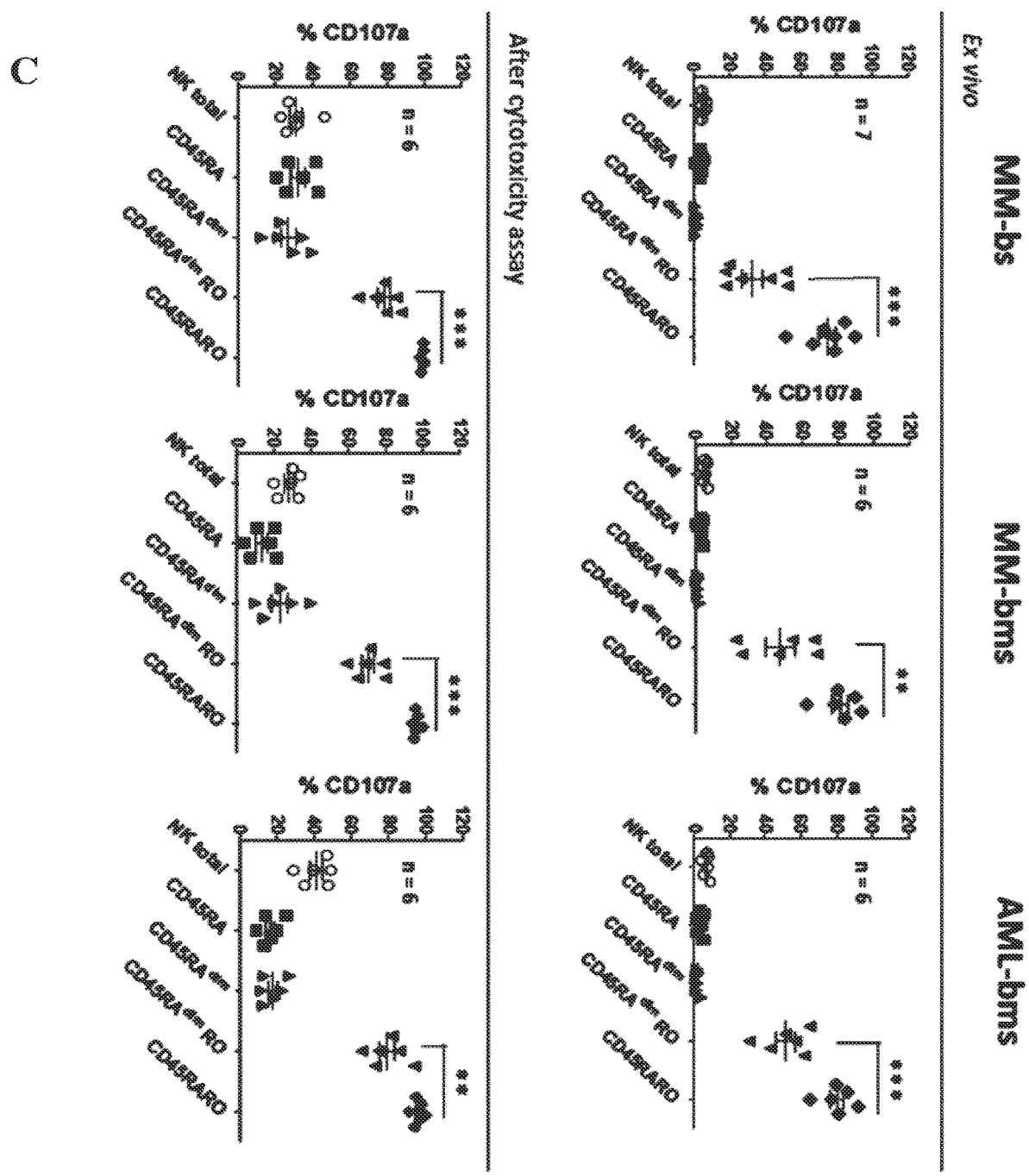

FIGS. 8A-8C. CD45 RARO identifies degranulating NK cells. PBMCs from healthy donors (HD) and patients with different hematological malignancies were purified. 8A) Number of CD107a$^i$ cells in each NK cell subset (CD45RA/RO expression) per million of NK cells. Bars represent the mean±SD for each medical condition; student t-test compare to healthy donor samples. 8B) Percentage of CD107a$^+$ NK cells in the four different subsets. 8C) Upper panels, Percentage of CD107a$^+$ cells in different NK cell subsets isolated from bone marrow samples (bms) of patients with MM (shown also the percentage in the corresponding blood sample, bs, for comparison) or AML. Bottom panels, Percentage of CD107a$^-$ cells in different NK cell subsets after exposure to target K562 tumor cells (in vitro cytotoxicity assay). PBMCs were incubated for 4 hours with target K562 tumor cells at the effector: target ratio of 10:1.

Figure 9:
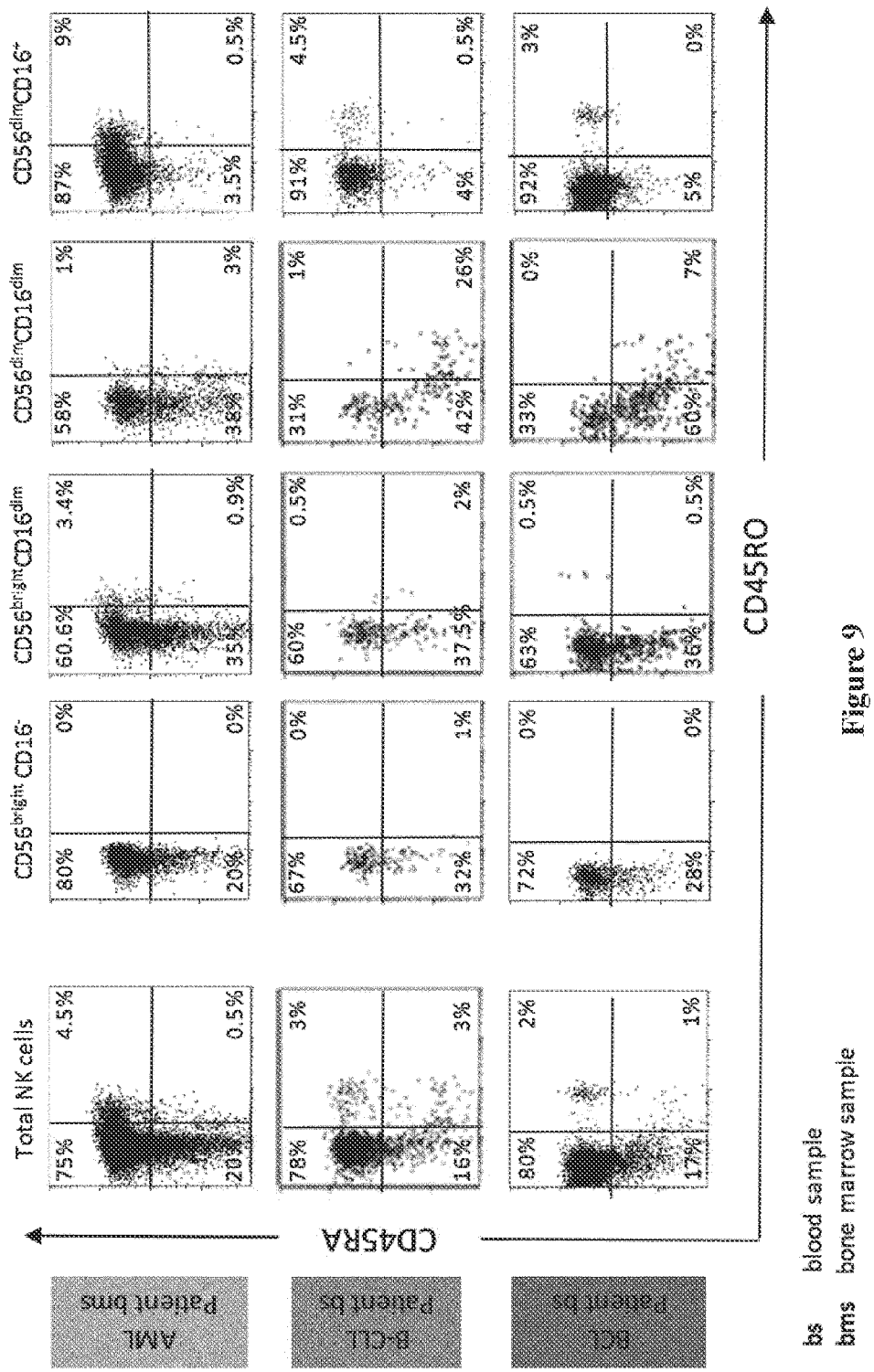

FIG. 9. NK cell subsets are modulated in patients with blood-borne cancers. PBMCs from patients with different hematological malignancies were stained with antibodies against CD45RA, CD45RO, CD56 and CD16 and analyzed as in FIGS. 3A-3D. The percentage of NK cells expressing the different CD45 isoforms is shown in the graphic. B-CLL, B-cell chronic lymphocytic leukemia; BCL, B-cell lymphoma; AML, acute myeloid leukemia; bs, blood samples; bms, bone marrow samples.

Figure 10:
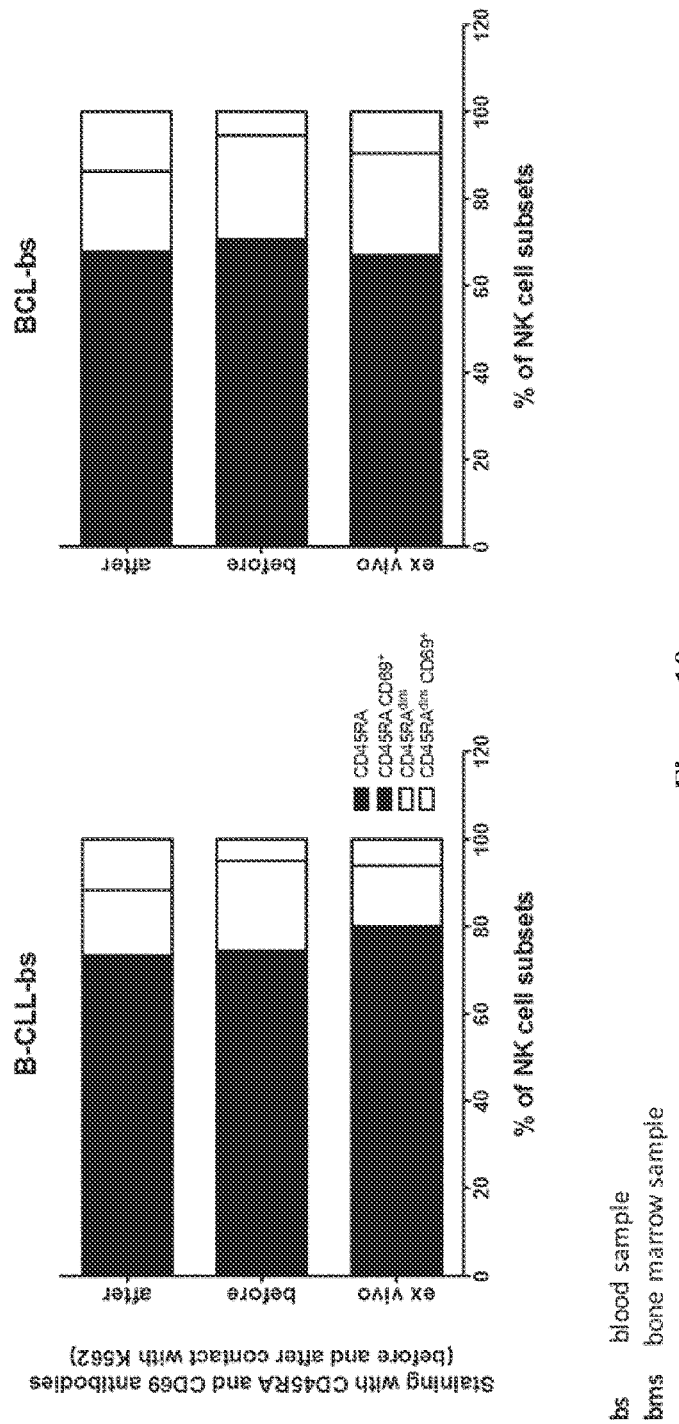

FIG. 10. CD45RA$^{dim}$ cells gain CD69 expression after in vitro activation. PBMCs isolated from blood samples were incubated for 4 hours with target K562 tumor cells at the effector:target ratio of 10:1. PBMCs were labeled ex vivo, at the end of the in vitro cytotoxic assay (after) or before the assay (before) with antibodies against CD45RA and CD69. The percentage of cells in each NK cell subset (based on CD45RA and CD69 expression) is shown; representative data from two patients with B-cell chronic lymphocytic leukemia (B-CLL) or B-cell lymphoma (BCL).

Figure 11:
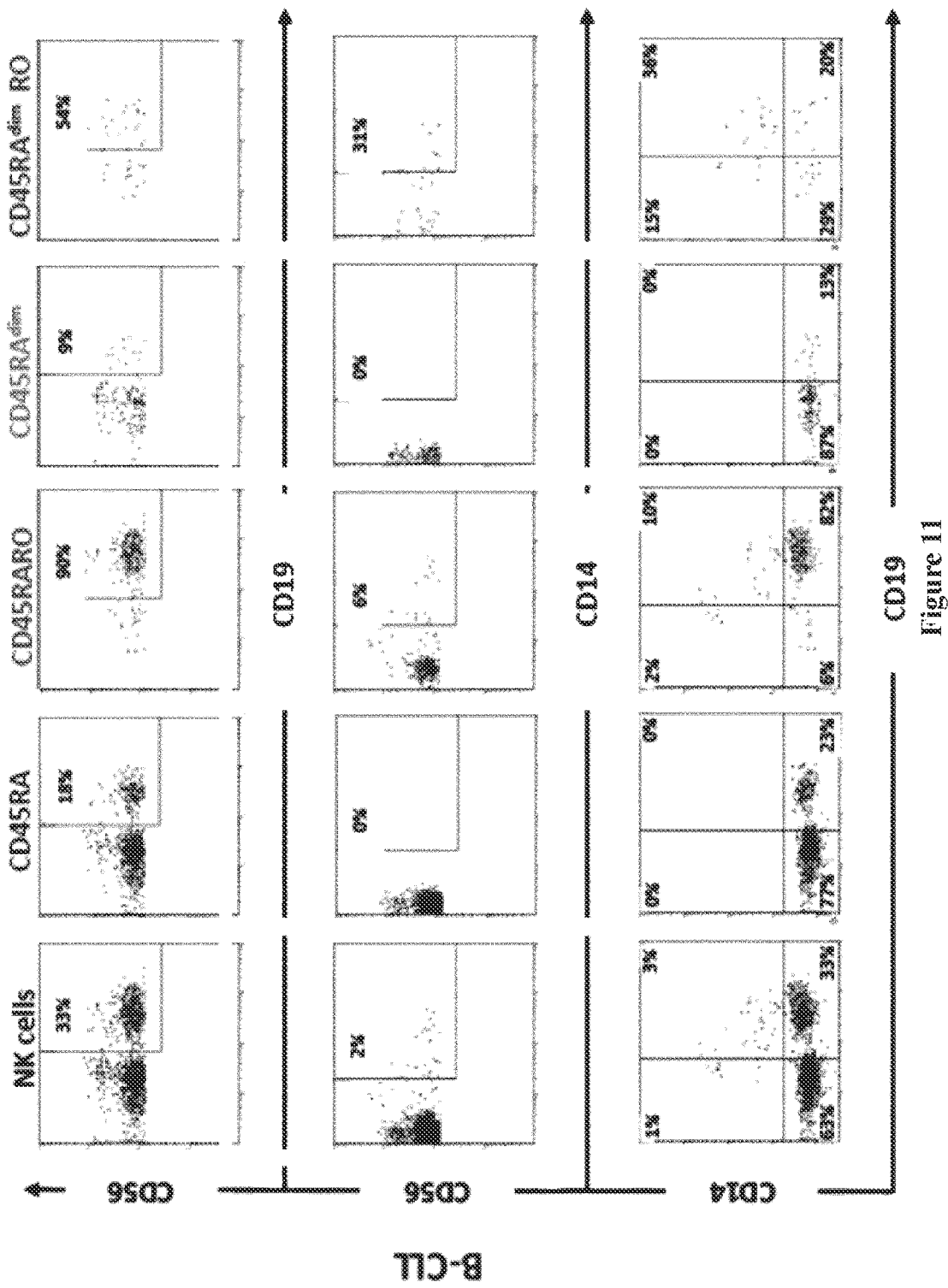

FIG. 11. CD45 RARO cells have performed trogocytosis on tumor cells in a B-CLL patient. PBMCs from a B-CLL patient were purified and were stained with different antibodies. In this experiment, the NK cell population corresponded to CD56$^+$NKP46$^+$ cells. The percentage of cells in each NK cell subset regarding CD45RA/RO is depicted in the graphics.

EXAMPLE

Material & Methods:

Cell Culture

The K562 cell line (ATTC CCL 243) was maintained in logarithmic growth in RPMI 1640 medium (Gibco® GlutaMAX™ media) with 10% fetal bovine serum (FBS) (Gibco®). Cells were cultured at 37° C. in a humidified chamber with 5% $CO_2$ in air, and passaged 1:10 twice a week. Bone marrow and peripheral blood samples were obtained from patients with different hematological diseases and from healthy donors after informed consent. Cells were purified by Ficoll-Hypaque (Sigma) density-gradient centrifugation. Primary cells were cultured in RPMI 1640 medium (Gibco® GlutaMAX™ media) supplemented with 10% FBS at 37° C. and 5% $CO_2$ in a humidified atmosphere.

Peripheral Blood Mononuclear Cell (PBMC) Purification

PBMCs were recovered using Histopaque-1077 (Sigma). Briefly, 3-6 ml of 1:2 diluted blood or 1:3 diluted bone marrow samples in RPMI were added on top of 5 ml of Histopaque. Cells were centrifuged at 1600 rpm and at 20° C. without break for 30 minutes. Mononuclear cells were collected from the interlayer white ring. After washing in RPMI, cells were suspended in complete RPMI medium supplemented with 10% FBS (Invitrogen).

Selection of Patients/Healthy Donors

Data and samples from patients with different hematological cancers were collected at the Oncology and Clinical Hematology Department of the CHU Montpellier, France, after patient's informed consent. Patients were enrolled in two independent clinical programs approved by the "Comités de Protection des Personnes Sud Méditerranée I (ref 1324)" and ID-RCB:2011-A00924-37.

Multicolor Staining of Cell Surface Markers

PBMCs were stained with 7AAD (Beckman) to identify viable cells and with the following anti-CD25-FITC, -CD45RO-FITC, -CD69-PE, -CD138-PE, -CD62L-PE, -CD19-PE, -CD3-PE, -CD19-ECD, -CD38-ECD, -CD56-PECy7, -CD56-APC, -CD3-APC, -CD45-APC AlexaFluor750, -CD45RA-APC AlexaFluor750, -CD16-PacificBlue, -CD57-PacificBlue, -CD45-KromeOrange, -CD16-KromeOrange (Beckman), -CD158b-FITC, -CD158a-PE, -CD107a-HV500, -Ki-67-V450 (BD Biosciences) and -CD71-APC (ImmunoTools) antibodies against surface markers for cell phenotyping. Briefly, 1×10$^6$ cells were incubated with the different antibodies in PBS/2% FBS at 37° C. for 30 minutes. Cells were then washed and suspended in 200-250 μl PBS/2% FBS and staining was analyzed using a Gallios flow cytometer (Beckman) and the Kaluza software.

Viable lymphocytes were gated using FSC/SSC and 7AAD staining. B lymphocytes (CD19+), T lymphocytes (CD3+CD56−) and NK cells (CD56+CD3−) were differentiated based on CD19, CD3 or CD56 expression. NK cells were then separated in four distinct populations based on CD45RA and CD45RO expression: CD45RA$^+$RO$^-$ (CD45RA), CD45RA$^+$RO$^+$ (CD45 RARO), CD45RA$^{dim}$RO$^-$ (CD45RA$^{dim}$), CD45RA$^{dim}$RO$^+$ (CD45RA$^{dim}$RO). These different populations were then analyzed for CD16, CD69, CD62L, CD57 and CD107a expression and cell size/granularity (FSC/SSC).

In vitro CD107a Degranulation Assay

After PBMC purification and NK cell quantification, 3 million cells were incubated at 37° C. for 4h with K562 target cells at a Effector (NK cell): Target ratio of 1:10 in a final volume of 500 μl (RPMI Glutamax with 10% FBS and 10 u/ml IL2). The medium also contained 1.5 μl anti- CD107a antibody (BD Biosciences, Franklin Lakes, N.J.) and 1 µl monensin to prevent CD107a degradation (BD Golgi-Stop BD Biosciences). Then, cells were resuspended in 50 µl of an antibody cocktail containing the anti-CD45RO-FITC, -CD69-PE, -CD19-ECD, -7AAD, -CD56-PECy7, -CD3-APC, -CD45RA-APCAlexaFluor750, -CD107a-HV500 and -CD16-KO antibodies (BD Biosciences, Beckman). In some experiments, PBMCs were incubated with anti-CD69 and -CD45RA antibodies also before exposure to target cells. Samples were analyzed on a Beckman Coulter FACS Gallios flow cytometer using the Kaluza software. Events were initially gated on forward and side scatter (SSC) to identify lymphocytes. A bivariate plot of CD56 versus CD3 was used to acquire at least 10,000 NK cells.

Multicolor Staining for Cell Surface and Intracellular Markers

After PBMC purification, 1 million cells were pre-blocked by incubation with 10% normal human serum at RT for 15 min and then stained with 50 µl of the PANEL Ki-67 antibody cocktail against cell surface markers (anti-CD45RO-FITC, -CD69-PE, -CD19-ECD, -CD3-PE-Cy5.5, -CD56-APC, -CD45RA-APCAlexaFluor750, -Ki-67 and -CD16-KO antibodies) (BD Biosciences, Beckman). Cells were washed twice with Staining Buffer and resuspended in 250 µl BD Cytofix/Cytoperm solution at 4° C. for 20 min. Cells were washed twice in BD Perm/Wash solution. Next, cells were fixed/permeabilized in 50 µl Perm/Wash solution containing an antibody cocktail against intracellular markers as described in the figures at 4° C. for 30 minutes in the dark. Cells were washed twice in BD Perm/Wash solution and resuspended in Staining Buffer prior to flow cytometric analysis on a Beckman Coulter FACS Gallios flow cytometer using the Kaluza software. Events were initially gated on forward and side scatter (SSC) to identify lymphocytes. A bivariate plot of CD56 versus CD3 was used to acquire at least 10,000 NK cells.

EBV Cell culture:

The K562 cell line (ATCC CCL 243) and the lymphoblastoid EBV cell line PLH (IHW Number: 9047) were maintained in logarithmic growth in RPMI 1640 medium (Gibco® GlutaMAX™ media) with 10% fetal bovine serum (FBS) (Gibco®). Cells were cultured at 37° C. in a humidified chamber with 5% $CO_2$ in air, and passaged 1:10 twice a week.

Identification of Pure Single NK Cells

Primary CD56+ NK cells were enriched and purified from PBMCs of B-cell lymphoma patients with the CD56+ NK cell isolation kit (Miltenyi Biotec, Auburn, Calif., USA). The purity (% of CD56+CD3−) of CD56+ NK cells, measured by flow cytometry, was >90%. Purified CD56+ NK cells have been stained with anti-CD335(NKp46)-PE to formally identify NK cells together with anti-CD45RA-FITC, -CD45RO-APC and -CD19-VioBlue (detection of trogocytosis-capable NK cells). Purified and stained NK cells have been analyzed with the DEPArray™ System (Silicon Biosystems, Menarini). This new technology allowed us to detect, enumerate and take pictures of single cells.

DEPArray™ Procedure

Cell sorting experiments were performed as described in the manufacturer's instructions and in (Lianidou et al., 2013). Briefly, DEPArray cartridges were manually loaded with 14 µl of sample and 800 µl of the buffer solution in which purified and stained NK cells had to be recovered. After loading the cartridge into the DEPArray system, ~9.26 µl of sample was automatically injected by the system into a microchamber of the cartridge where the cells were spontaneously organized into a preprogrammed electric field consisting of 16000 electrical cages in which individual cells are trapped. Image frames covering the entire surface area of the microchamber for each of four fluorescent filter cubes (FITC, PE, APC and DAPI/Hoechst/VioBlue/PacificBlue) and bright field images were captured. Captured images were digitally processed and presented in a software module that enables selection of cells of interest by the operator.

In Vitro NK Cell Stimulation Protocol

PBMCs, $1.10^6$ cells/ml, were stimulated during 10 or 20 days with a high dose of IL-2 (1000 U/ml, eBiosciences) or with the lymphoblastoid EBV cell line PLH together with IL-2 (100 U/ml) and IL-15 (5 ng/ml, Miltenyi).

Statistics

All the experiments shown in the figures were performed at least with samples from six patients for each malignancy and the same number of healthy donors.

Results:

CD45 is a Marker of Mature Human NK Cells

To determine whether high CD45 expression is a marker of cell maturation also in human NK cells like in other lymphocyte types (26), we analyzed CD45 expression in the three main types of human lymphocytes (T, B and NK cells) derived from PBMCs. B and T cells showed relatively homogenous populations with comparable levels of CD45 expression. $CD56^{bright}$ (thus relatively immature) NK cells showed lower total CD45 expression, in agreement with the notion that CD45 is a marker of lymphocyte maturation. Most NK and B cells expressed CD45RA, whereas very few expressed CD45RO. In contrast, a large T cell population expressed CD45RO instead of CD45RA.

We then analyzed the association of total CD45 expression with known NK cell markers. CD45 expression in NK cells was associated with expression of the KIRs CD158a and CD158b and of CD16 (markers of NK cell maturation (14, 34)). Conversely, CD45 expression was lower in cells positive for CD25 (a marker of cell proliferation). CD45-positive cells also expressed more frequently CD69, which is associated with NK cell cytolytic activity (35), than CD45-negative cells. These results indicate that in NK cells, total CD45 expression is mainly associated with high expression of NK cell maturation markers, such as CD16 and KIRs, and low expression of CD56 and CD25 (markers of immature NK cells).

Expression of Different CD45 Isoforms In Vivo: Healthy Donors

The previous results indicate that few NK cells express CD45RO compared to T cells. A more detailed analysis of cell surface marker expression in NK cells from healthy donors showed that the vast majority of NK cells were CD45RACD69⁻ cells and only 5% of them expressed CD69. Among the 4% of NK cells with low CD45RA expression ($CD45RA^{dim}$, only 1% was CD69+. Furthermore, based on the expression of CD56 and CD16, CD45RA+RO⁻ (CD45RA) cells could be considered fully mature cells, whereas $CD45RA^{dim}RO^-$ ($CD45RA^{dim}$) cells were consistently found in immature populations. The very few CD45RA+RO+ (CD45 RARO) cells were $CD56^{dim}CD16^+$, whereas $CD45RA^{dim}RO^-$ ($CD45RA^{dim}RO$) cells were $CD56^{dim}CD16^{dim}$. These results suggest that CD45RA and CD45RO expression are associated with NK cell maturation in healthy donors.

Expression of Different CD45 Isoforms In Vivo: Allografted Patients We then investigated the NK cell profiles in allografted patients in whom the NK cell population was reconstituted from donor hematopoietic stem cells. In these patients, CD45RO and/or CD45RA$^{dim}$ NK cells were more abundant than in healthy controls, generating a comet-like shape when both markers were plotted in a graph. As expected, in blood samples from allografted patients, the number of immature NK cells was larger than in healthy controls, based on CD56 and CD16 expression. These CD56$^{bright}$ cells were CD16$^-$, suggesting that they were de novo produced NK cells and not CD56$^{dim}$ cells that gained CD56 expression following activation. During in vivo maturation CD56$^{bright}$ cells become CD56$^{dimCD}$62L$^+$CD57$^-$ cells that produce perforin, while maintaining high IFN-γ production in response to cytokines (12, 36). Then, CD56$^{dim}$CD62L$^-$CD57$^+$ cells show low response to cytokines and higher cytotoxic capacity (12, 37). Indeed, independently of CD16 expression, CD62L expression was higher in CD56$^{bright}$ cells than in CD56$^{dim}$ cells in allografted patients. And the density of CD57 expression was higher in CD56$^{dim}$ cells than in CD56$^{bright}$ cells. Moreover, all NK cell populations from allografted patients were enriched in CD45RA$^{dim}$ and CD45RO cells compared to healthy donors. However, the percentage of CD45RA$^{dim}$ cells progressively decreased in more mature NK cell subsets as observed in healthy donors.

Expression of Different CD45 Isoforms In Vivo: Patients with Hematological Malignancies The previously described patients were grafted with bone marrow as a treatment for different hematological cancers. In all these patients, CD45RO and/or CD45RA$^{dim}$ NK cells were more abundant than in healthy controls. In particular, some CD45RA cells were also CD45RO$^+$. We thus hypothesized that in addition to a population of immature NK cells with reduced CD45RA expression, some NK cells could have been activated by target tumor cells. We thus investigated the NK cell profile of patients with different hematological malignancies.

Figure 3A:
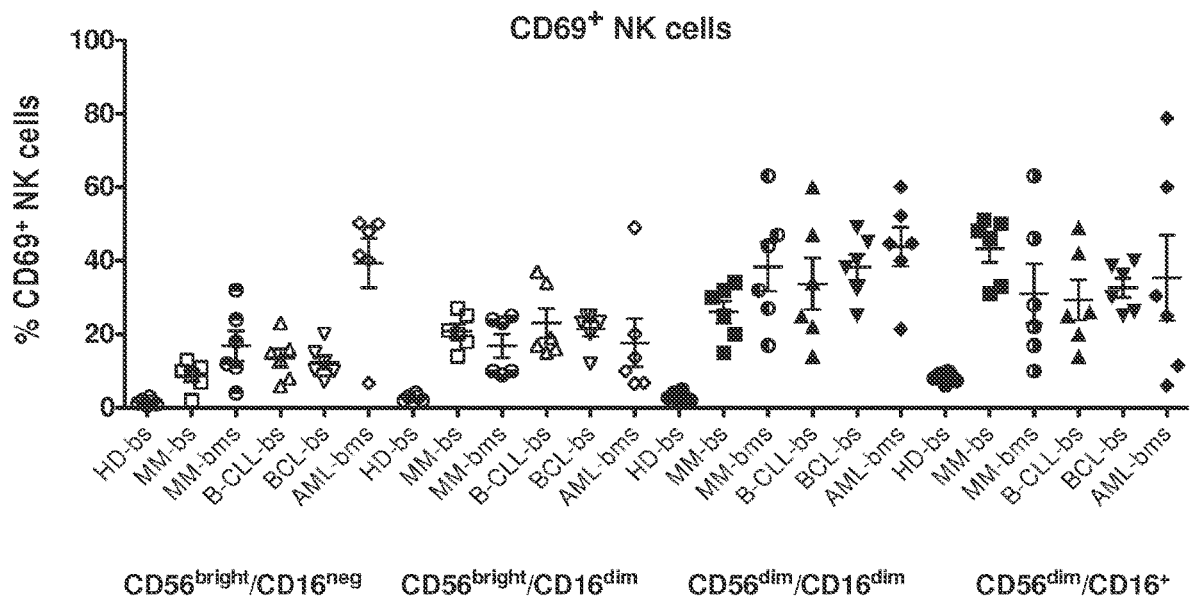

As previously described in healthy donors, NK cells were mainly mature CD45RA cells with few CD45RA$^{dim}$ cells, found particularly in immature NK cell subsets. CD45 RARO cells represented around 0.2% of all NK cells (FIG. 1A top panels). Blood samples from patients with multiple myeloma (MM) contained four times more CD45RA$^{dim}$ cells and about 5% of CD45RO cells that, surprisingly, generally maintained CD45RA expression (FIG. 3A middle panels). As MM is characterized by accumulation of tumor cells in the bone marrow, we also investigated whether bone marrow NK cells, which should be in closer contact with tumor cells, were more activated than circulating NK cells. This was not the case as the percentage of CD45RA$^{dim}$ and CD45RO cells was similar in blood and bone marrow samples (FIG. 1A, middle and lower panels).

Figure 1B:
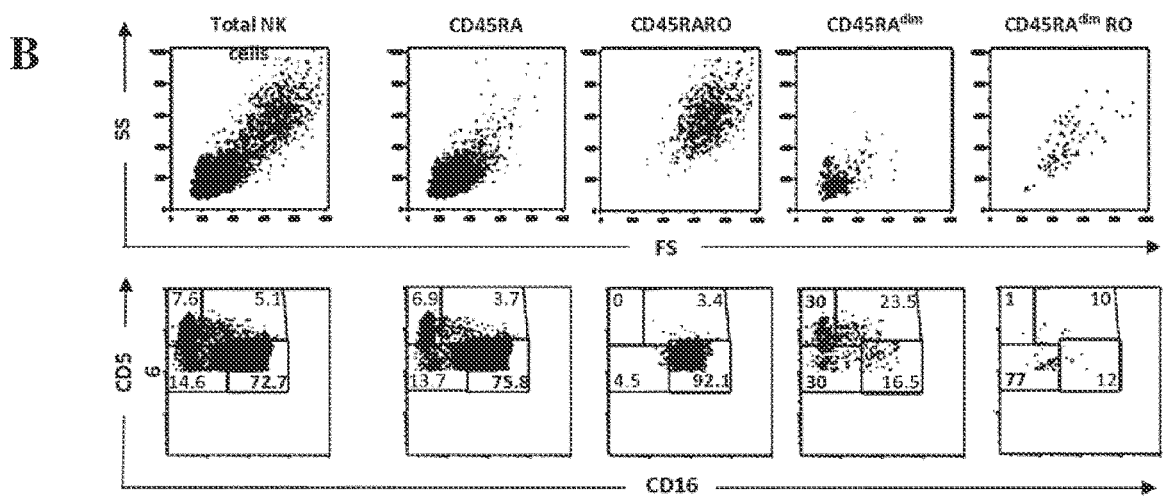

Moreover, a subset of NK cells from MM patients was larger in size (FS) and with high granularity (SS) (FIG. 1B). This population corresponded mainly to CD45 RARO cells that belonged almost exclusively to the CD56$^{dim}$CD16$^+$ subset (FIG. 1A and FIG. 1B bottom panels). The large size (FS) and granularity (SS) of these CD45 RARO cells suggest that they have a higher metabolic activity compared to the other NK subsets, although size and granularity were slightly increased also in CD45RA$^{dim}$RO cells (mainly CD56$^{dim}$CD16$^{dim}$) (1B). Conversely, CD45RA$^{dim}$ cells had low FS and SS values and were clearly enriched in the immature compartments.

Figure 1C:
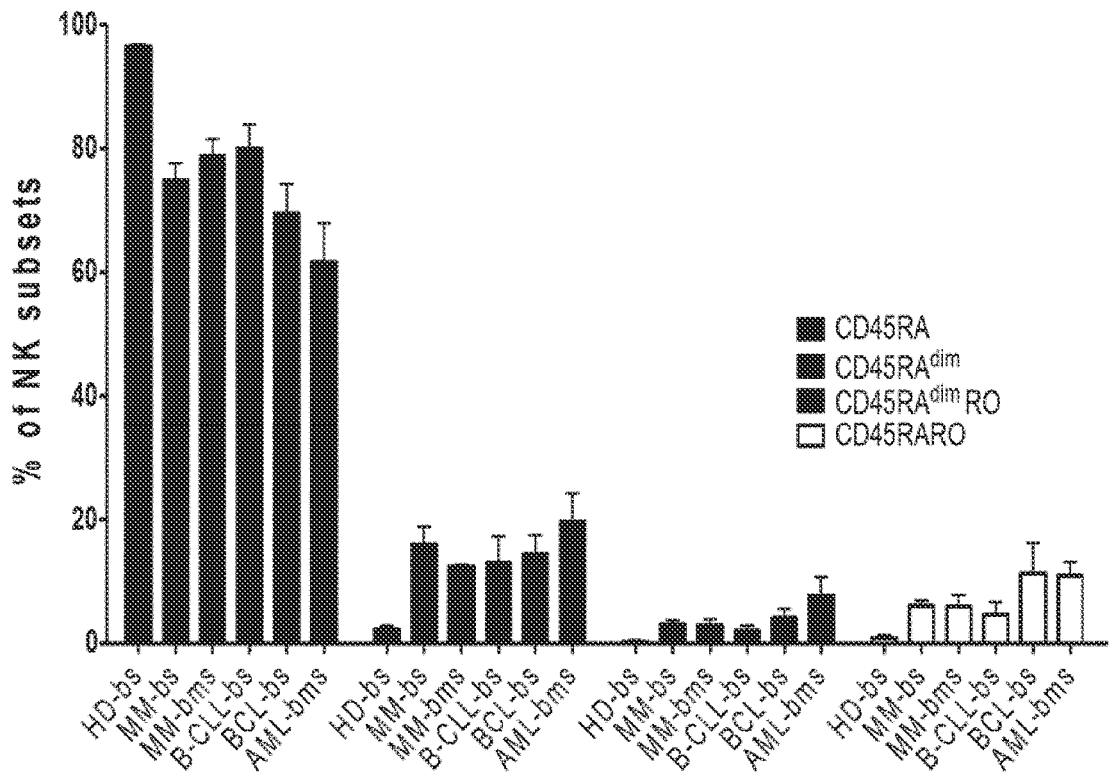

Similar increases in the CD45RA$^{dim}$ and CD45RO populations were observed also in blood samples from patients with other hematological cancers, such as acute myeloid leukemia (AML), B-cell chronic lymphocyte leukemia (B-CLL) and B-cell lymphoma (BCL) (FIG. 9). In summary, the CD45RA population was reduced, whereas the CD45RA$^{dim}$, CD45RA$^{dim}$ RO and C45 RARO cell fractions were increased in all analyzed samples from patients with blood malignancies compared to healthy controls (FIG. 1C).

Figure 1D:
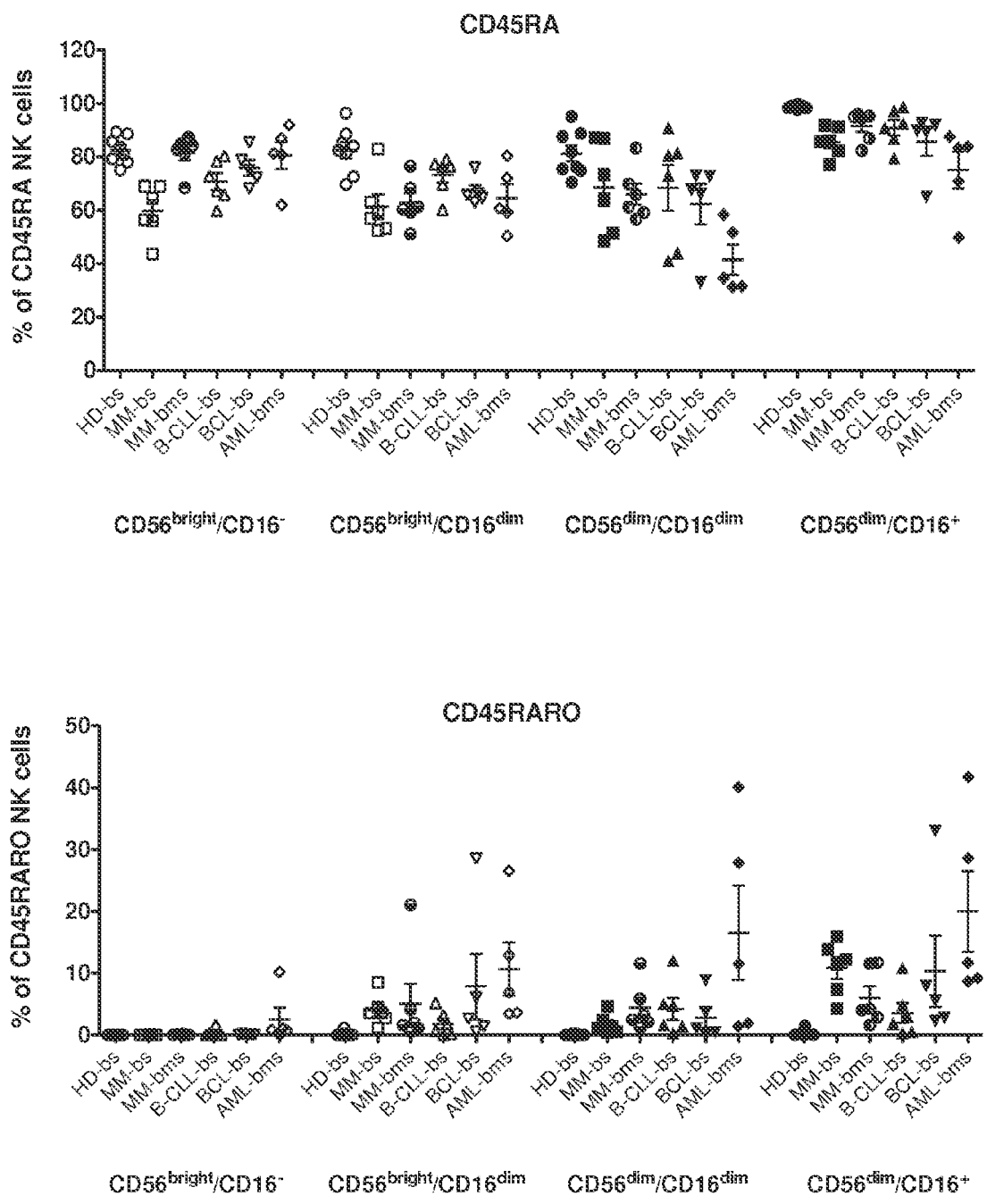
Figure 1D:
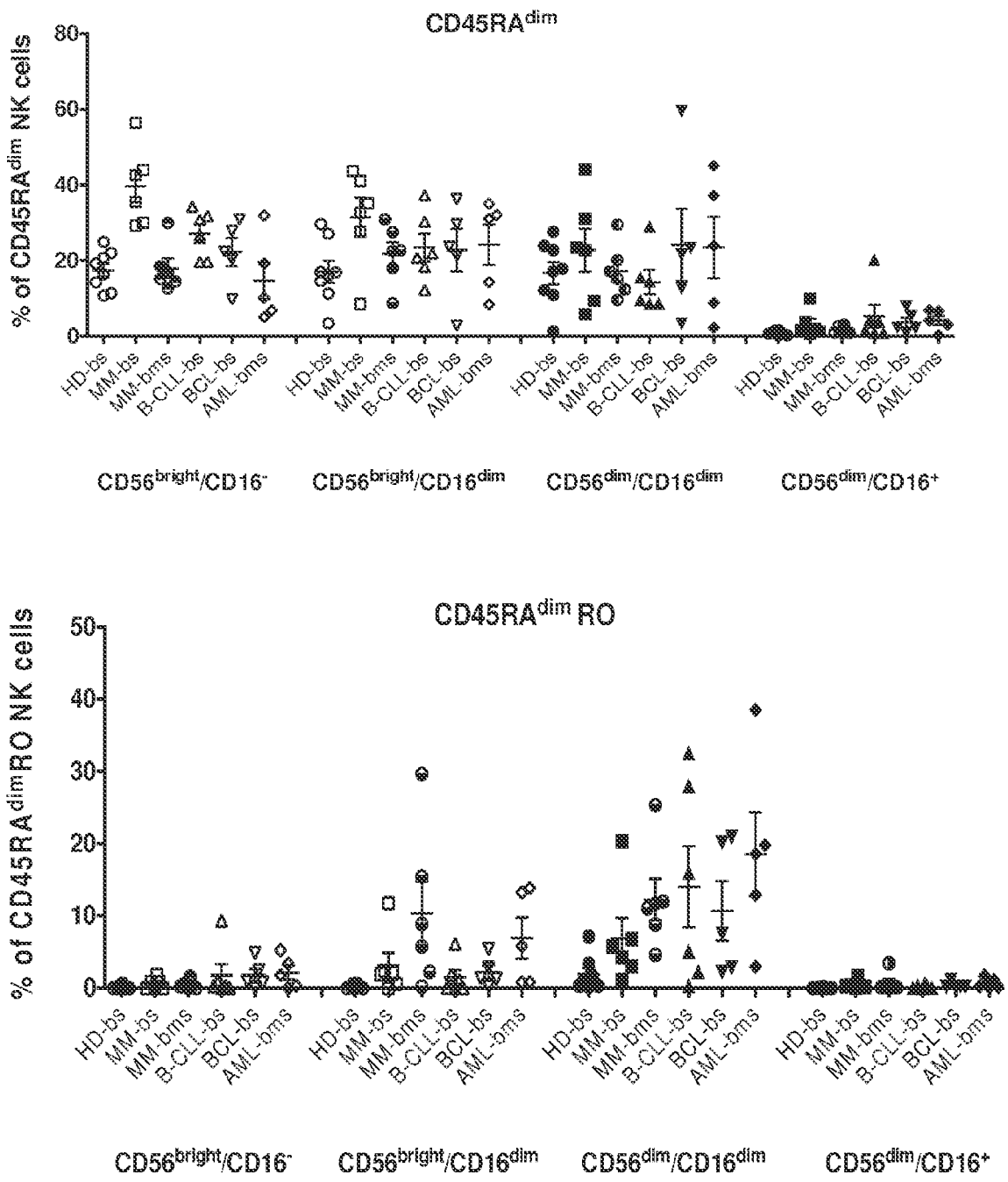

Finally, we quantified the expression of the different CD45 iso forms at the four NK cell developmental stages (based on CD56/CD16 expression) in samples from patients with blood cancers and healthy donors (FIG. 1D). In healthy donors the immature compartments contained 15% of CD45RA$^{dim}$ cells, whereas this population was basically absent in the fully mature subset of NK cells. However, CD45 RARO cells were exclusively found in the mature compartment. In all patients with hematological cancers (independently of the tumor type) the number of CD45RA$^{dim}$ cells in the mature NK cell compartment was increased. CD45RA$^{dim}$RO cells were increased in the immature compartments and CD45 RARO cells were strongly increased especially in the most mature NK cell subset. In fact, the strong increase of CD45RA$^{dim}$ and CD45 RARO populations in the CD56$^{dim}$CD16$^+$ NK cell subset from patients with hematological cancers clearly distinguished them from healthy donors and could be used as a diagnostic tool.

Expression of Different CD45 Isoforms In Vivo: Patients with CMV-Reactivation

We next asked whether other conditions that lead to NK cell activation, such as viral infections, could give rise to a similar phenotype. We thus analyzed PBMC samples from patients with reactivation (CMV+) or not (CMVneg) of CMV infection following kidney transplantation. CMV reactivation induced an increase in the total number of NK cells (FIG. 2A). In addition, CMV+ patients showed an increase in CD56$^{dim}$CD16$^{dim}$ cells associated with a reduction of the CD56$^{bright}$ subsets compared to CMVneg patients (FIG. 2B). The reason of these changes is not clear to us, but could be due to different factors, such as CMV-induced NK cell maturation (38), or an effect on the expression of the different NK cell markers in CMV-infected cells, as previously described for decidual NK cells (39). These changes were accompanied by minor variations in the expression pattern of CD45 isoforms, mainly an increase in CD45RA$^{dim}$ cells that expressed also CD69 and CD45RO (FIG. 2C). These results indicate that the expression pattern of CD45 iso forms in NK cells activated by viral infection or hematological cancers is different. Specifically, CD45 RARO cells are mainly present in samples from patients with hematological cancers, whereas they represent a minor fraction in allografted or virus-infected patients.

Relationship Between CD45 Isoforms and CD69 Expression

Figure 3B:
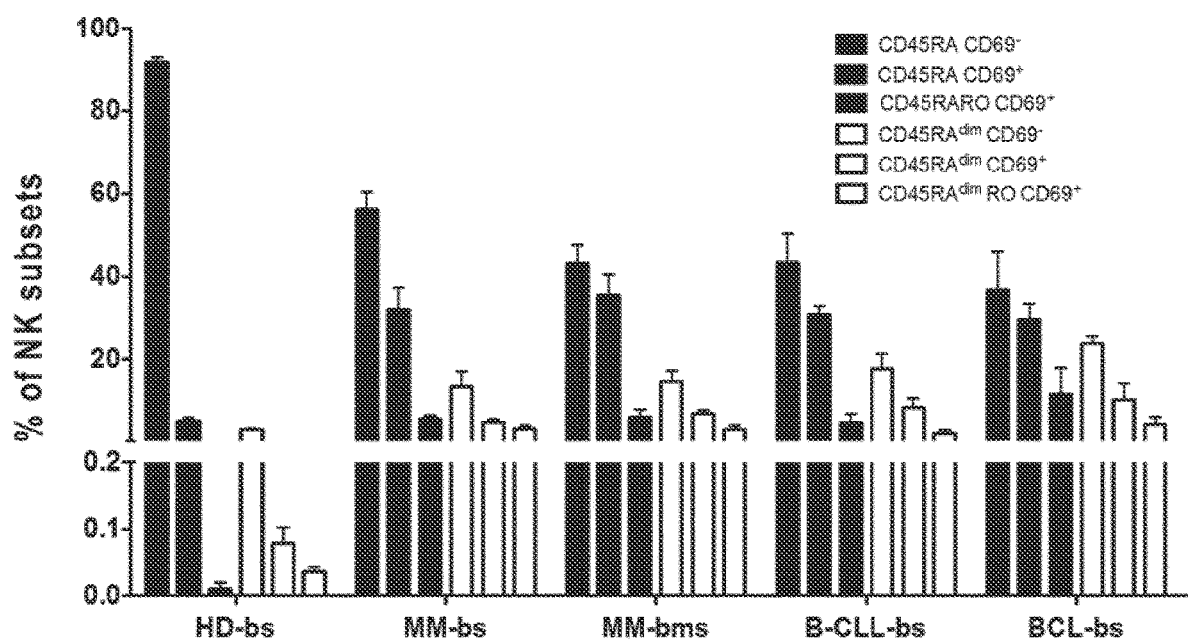
Figures 3C, 3D:
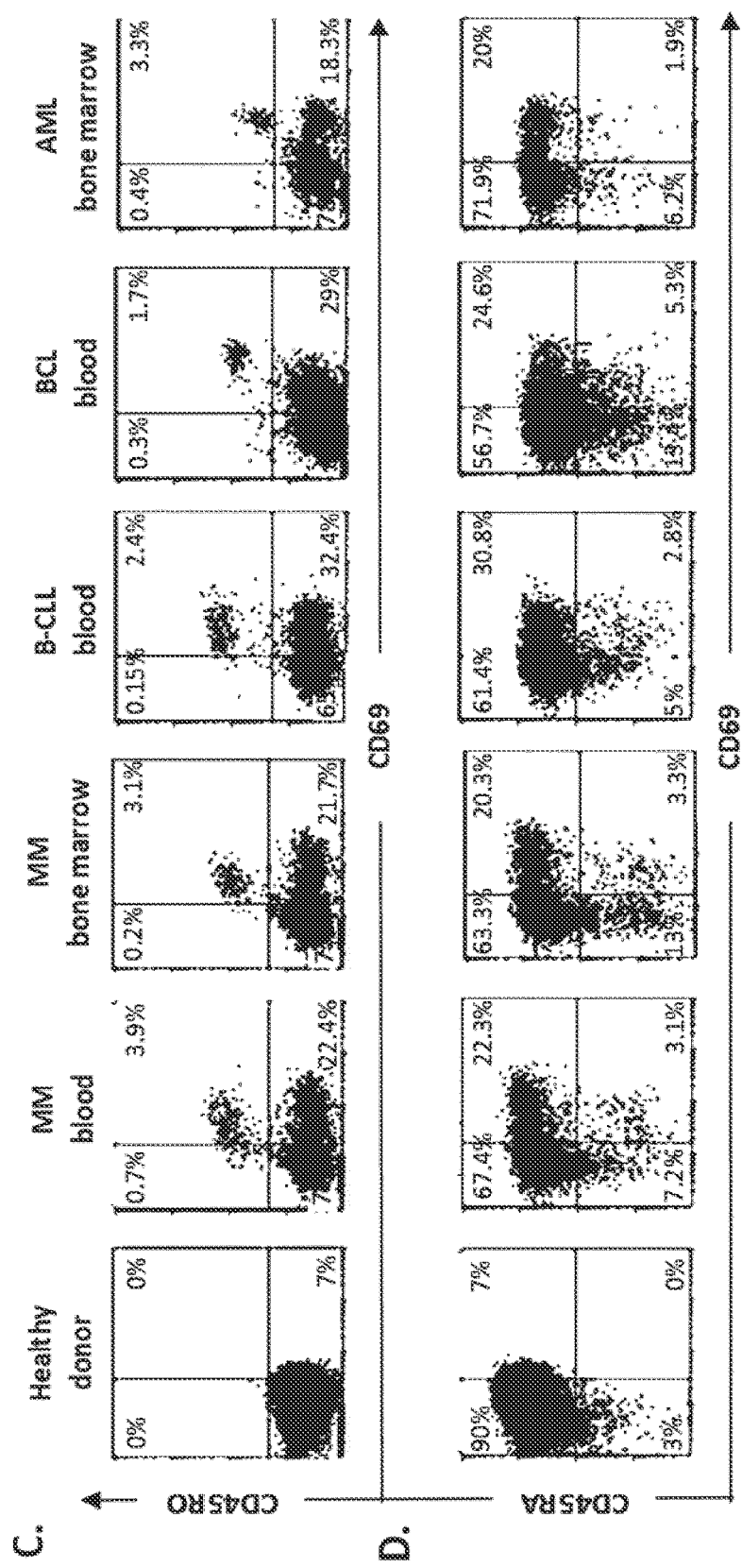

CD69 expression increases after NK cell stimulation and is considered a bona fide marker of NK cell activation (17), including in vivo (6). In healthy donors, CD69 was mainly expressed by fully mature CD56$^{dim}$CD16$^+$ cells (FIG. 3A), whereas in patients with hematological malignancies CD69$^+$ cells were detected also in other NK cell subsets (FIG. 3A). Indeed, in such patients, CD69 expression was observed in all NK subsets, independently of their maturation, compared to healthy donors (FIG. 3B). Analysis of CD69 expression in the different CD45 populations in patients showed the presence of larger amounts of CD45RA and CD45RA$^{dim}$ cells that co-expressed also CD69 and CD45RO compared to healthy controls (FIGS. 3B and C). CD45RO$^+$ cells were mainly CD69$^+$ (FIG. 3C); however, the opposite was not true as most CD69$^+$ cells were not CD45RO. The very low amount of CD45RO$^+$ cells in healthy donors precluded any meaningful analysis of this population.

In healthy donors, CD45RA$^{dim}$ cells were mainly CD69$^-$ (FIGS. 3B and D). CD45RA$^{dim}$ cells were significantly increased in patients and many were also CD69$^+$. However, reduction of CD45RA expression was not always associated with gain of CD69 expression. In fact, patients' samples were enriched particularly in CD45RA$^{dim}$ CD69$^-$ and CD45RA CD69$^+$ and, to a lower extent, in CD45RA$^{dim}$ CD69$^+$ cells. As blood samples from patients with AML were not available, we used bone-marrow (bm) samples and obtained similar results (FIGS. 3 C and D). Bone marrow from patients with MM displayed a similar pattern. Unfortunately, we could not analyze bone marrow samples from healthy donors and thus we cannot firmly conclude that the NK cell profiles in bone marrow samples from patients with hematological malignancies and healthy donors are different, like for blood samples. However, the finding that the NK cell populations are similar in blood and bone marrow samples from patients with MM suggests that the healthy donor-patient differences found in blood are also present in bone marrow.

In conclusion, patients showed an increase in CD69 expression in all NK cell subsets, but the relative percentage of CD69$^+$ cells was higher in CD45RA than in CD45RA$^{dim}$ cells (FIG. 3B). These data suggest that CD69 up-regulation together with CD45RA down-regulation and CD45RO up-regulation is compatible with NK cell activation. CD69$^+$ cells were mainly in the terminally differentiated CD56$^{dim}$CD16$^+$ subset (FIG. 3A) whereas CD45RA$^{dim}$ cells were mostly in immature populations (CD56$^{bright}$ and CD56$^{dim}$CD16$^{dim}$). This finding suggests that loss of CD45RA and gain of CD69 expression identify two different physiological processes and that these two populations might have different functions. Conversely, CD69 expression in the different NK cell subsets did not improve the identification of patients with hematological malignancies compared to the expression of CD45 isoforms.

Figure 4A:
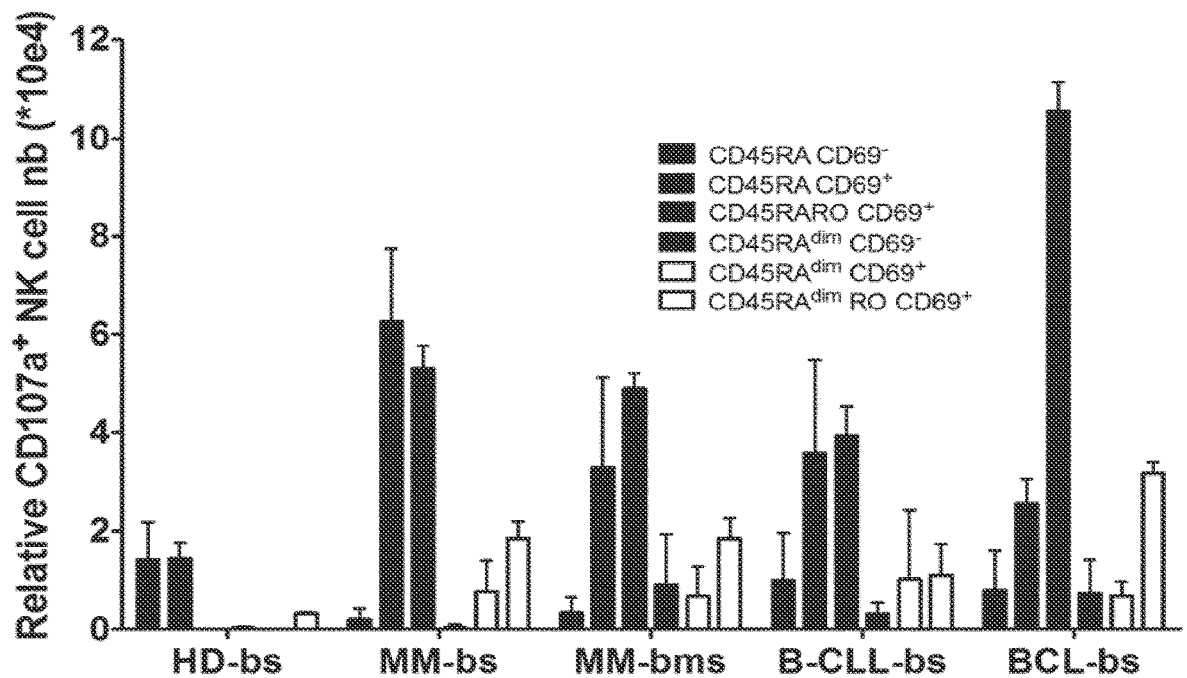
Figure 4B:
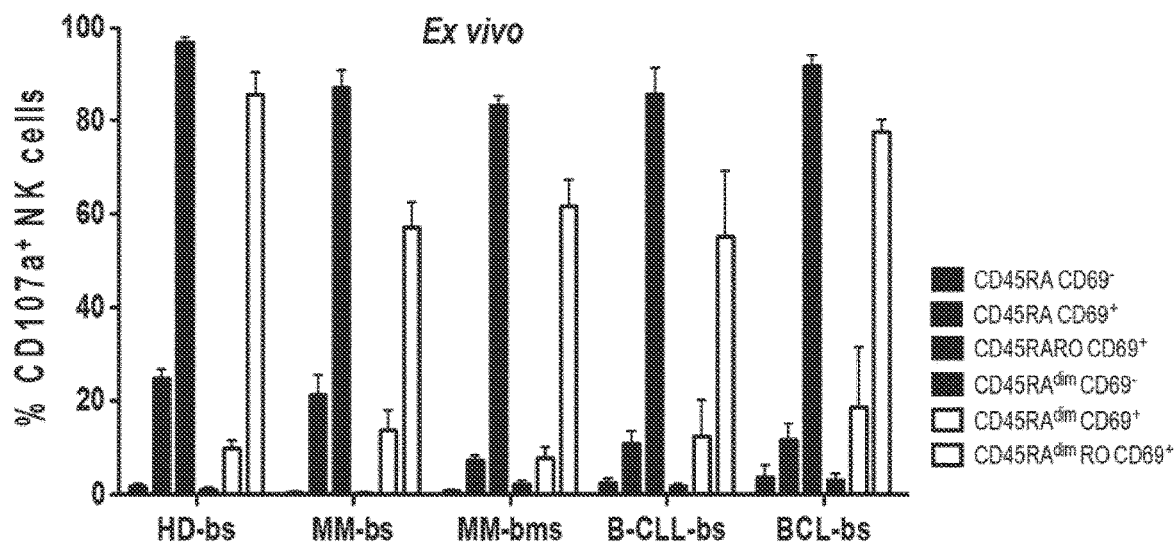

Expression of Different CD45 Isoforms Identifies Different NK Cell Functions Ex Vivo To identify the function of the different NK cell subsets, first we assessed cell degranulation by ex vivo staining of PBMCs with anti-CD107a antibodies (FIG. 4A). In healthy donors, around 40×10$^3$ cells/million NK cells were CD107a$^+$. Most of these cells were CD45RA, either CD69+ or −, with a small number of CD45RO$^+$ cells. Remarkably, all CD45 RARO and most of CD45RA$^{dim}$RO cells were CD107a$^+$ (FIG. 4B). Overall, CD107a expression was observed more in CD69$^+$ than in CD69$^-$ cells and CD45RA down-regulation was not associated with CD107a expression acquisition.

Figure 4C:
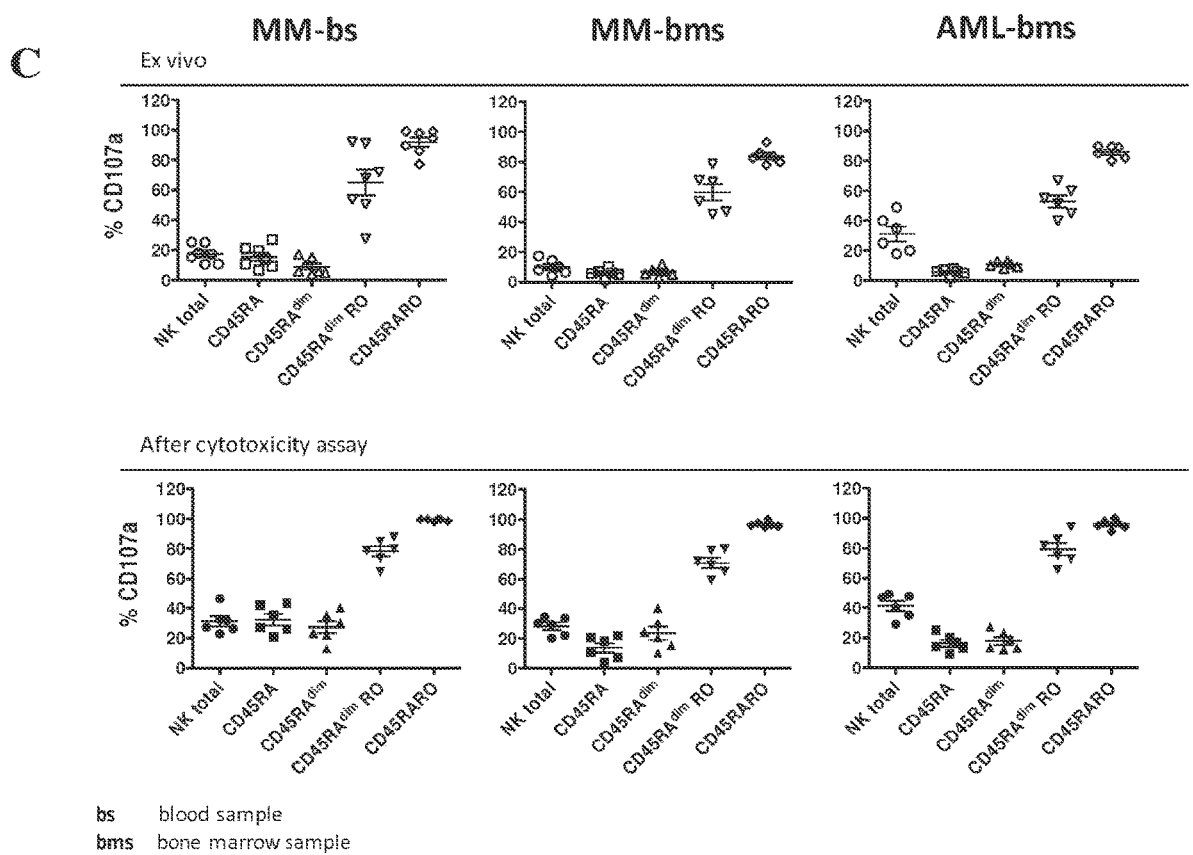

NK cells from patients with hematological cancers showed a large increase in CD107a$^+$ cells (FIG. 4A), particularly among the CD69$^+$ and/or CD45RO$^+$ subsets, which are specifically increased in these patients. Moreover, the percentage of CD107a$^+$ cells was higher in the CD69$^+$ than in CD69$^-$ subsets, whereas reduction of CD45RA expression was not associated with increased degranulation (FIG. 4B). Like in healthy donors, the CD45 RARO CD69$^+$ and, to a lower extent, CD45RA$^{dim}$RO CD69$^+$ fractions contained mostly cells that had degranulated. This was not exclusive of circulating NK cells, because similar results were obtained also for NK cells derived from bone marrow samples of patients with MM and AML (FIG. 4C upper panels).

Figure 4D:
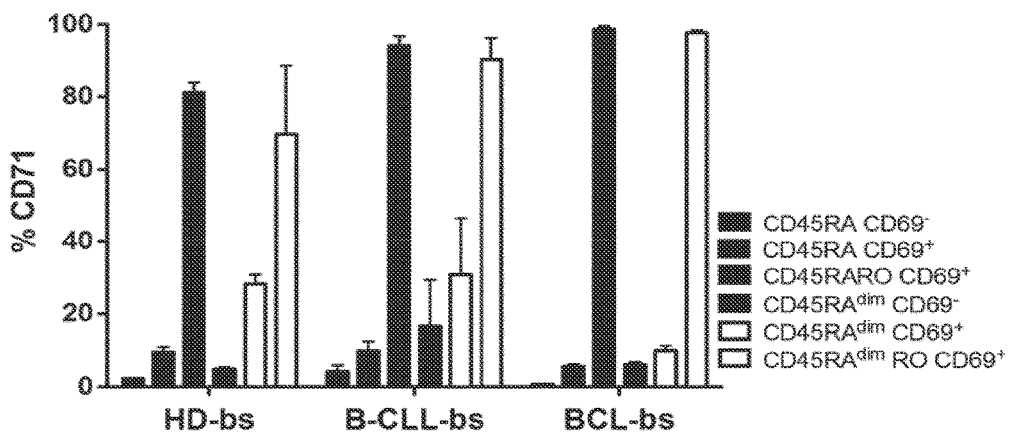
Figure 4E:
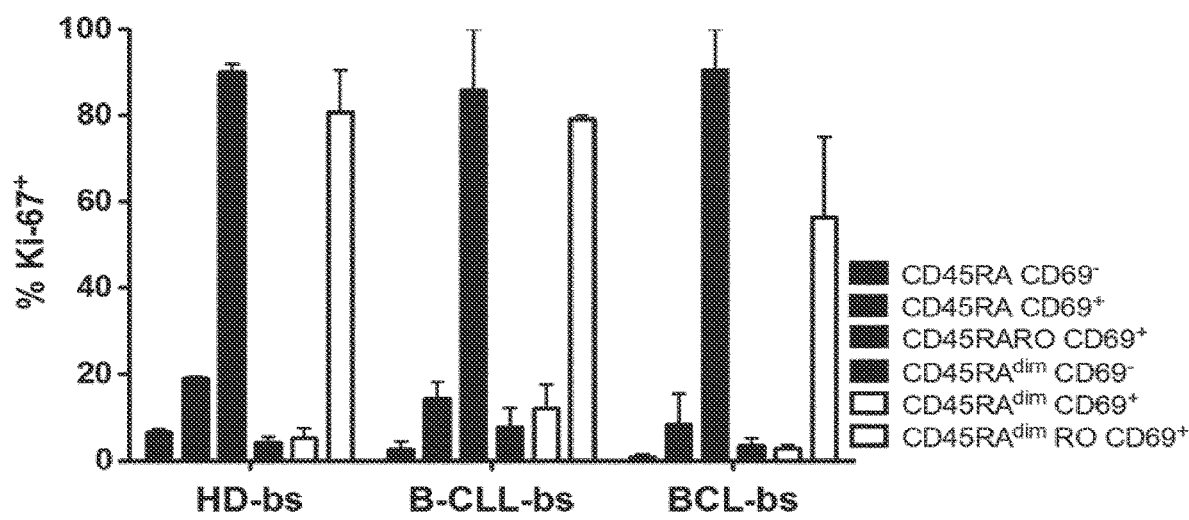

We then assessed the expression of transferrin receptor protein 1 (TfR1 or CD71), which is required for iron delivery from transferrin to the cells. CD71 expression increases in highly metabolic cells because iron is a cofactor for fundamental biochemical activities, such as oxygen transport, energy metabolism and DNA synthesis (40). In agreement with the high metabolic activity of CD45 RARO cells (FIG. 4B), CD71 expression was higher in CD45RO$_1$ cells in both healthy controls and patients with hematological malignancies (FIG. 4D). Moreover, most of these cells also expressed the proliferation marker Ki-67 (FIG. 4E). CD71 and Ki-67 expression were also moderately higher in CD69$^+$ than in CD69$^-$ subsets.

Altogether our results indicate that CD45RO$^+$ cells (particularly when they express also CD45RA) gain CD69 expression, are larger and with higher granularity and metabolism (FIG. 4D), proliferate (FIG. 4E) and degranulate (FIG. 4B). These findings suggest that CD45 RARO cells, and probably also CD45RA$^{dim}$RO cells, are the NK cells that recognize tumor cells and degranulate. CD45 RARO CD107a$^+$ cells mainly belong to the CD56$^{dim}$CD16$^+$ fraction, whereas CD45RA$^{dim}$RO CD107a$^+$ cells are mainly CD56$^{dim}$CD16$^+$ cells.

Other NK Cell Subsets from Patients with Hematological Cancers Show Cytolytic Activity Against K562 Cells In Vitro To investigate whether the other NK cell subsets from patients with hematological cancers have intrinsic defects in degranulation, we incubated PBMCs from healthy donors or patients with K562 target cells. In healthy donors, the number of degranulating CD45RO$^+$ cells, which was already high ex vivo, increased to almost 100%. The percentage of CD107a$^+$ cells increased also particularly in the CD45RA$^{dim}$ subset and in the CD69$^+$ subsets. Similarly, all NK cells populations from patients with hematological malignancies also retained the capacity to degranulate, particularly CD45RA$^{dim}$ cells.

However, in our analysis we could have under-evaluated the percentage of CD69$^-$ or CD45RA$^{dim}$ cells that degranulated because after four hours of incubation with target cells the expression of CD69 and/or CD45 isoforms might have changed. We thus incubated PBMCs first with anti-CD69 and -CD45RA antibodies to determine the basal NK cell phenotype, and then we analyzed CD107a expression after exposure to K562 cells (FIG. 10).

Figure 7A:
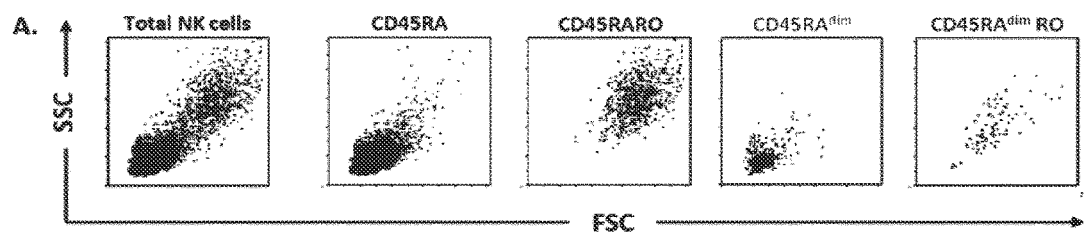
Figure 7:
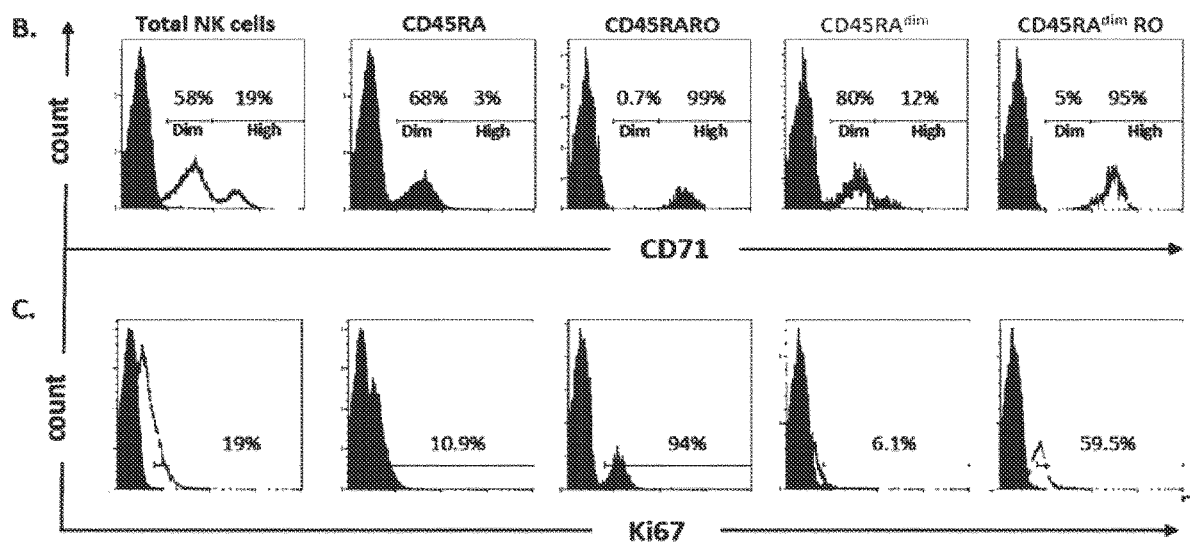

Indeed, the NK cell profile before contact with target cells was similar to the phenotype observed ex vivo, showing that this was an efficient approach. After in vitro incubation with target cells (4 hs), the number of CD69$^+$ cells rapidly increased both in the CD45RA and CD45RA$^{dim}$ populations (about 100% increase in both subsets). However, the overall percentage of CD45RA and CD45RA$^{dim}$ cells remained stable during this time (FIG. 10). We realized that degranulation of CD69$^-$ NK cells from healthy donors was higher than showed in FIG. 7A (FIG. 7C). Activated cells probably gained both CD69 and CD107a expression at the same time. This was more evident in NK cells from patients with hematological cancers in whom a large part of cells that degranulated were at the beginning CD69$^-$ cells. The CD45RA$^{dim}$ cells that gained CD69 expression after exposure to target cells were mainly CD56$^{dim}$ CD16$^{dim}$ and fully mature CD56$^{dim}$CD16$^+$. In summary, CD45RA$^{dim}$ cells also can respond to stimuli at least by gaining CD69 and CD107a expression.

CD45 RARO NK Cells have Performed Trogocytosis In Vivo

To investigate if CD45 RARO cells were performing antitumor activity in vivo, we investigated if these cells have performed trogocytosis on tumor targets. Trogocytosis is a process whereby lymphocytes extract surface molecules from interacting cells and express them on their own surface and has been observed in B lymphoblastic leukemia (B ALL) ex vivo. Because in this experiment we studied markers of other cell types, we used a double labeling to identify NK cells and gated on $CD56^+NKP46^+$ cells. We observed that 14% of NK cells from BCL patients express the BCL marker CD19 in their membrane (FIG. 5A). This value increased to 52% in the CD45 RARO population and it was much lower in the other populations. NK cells also gained at lower level expression of the myeloid marker CD14, although the population was predominantly $CD45RA^{dim}RO$. However, the NK cells that stained positive for both markers were very rare. This suggested that two different NK cell populations were performing trogocytosis and the CD45 RARO was doing it on tumor cells. We observed the very similar results in another $CD19^+$ disease: B-CLL (FIG. 11). To exclude that NK cells were not gaining CD19 in all tumors, we investigated NK cells from AML patients (FIG. 5B). Around 10% of NK cells expressed the AML marker CD14 and only 3% expressed CD19, which was expressed in all NK cell populations. In contrast, 90% of CD45 RARO expressed CD14 showing that they have massively performing trogocytosis in a $CD14^+$ population in AML patients. In summary, our data showed that NK cells performed trogocytosis on tumor cells and that the CD45 RARO population is responsible of this. Hence, the use of CD45 RARO NK cells can be used as a diagnostic tool to identify hematological cancer patients (if this population is present) and the kind of disease (the markers that express in the membrane).

Phenotypic Characterization of CD45 RARO Population

CD45 RARO cells belonged to the $CD56^+CD16^-$ subset and mostly express the maturation marker CD57 although CD62L was coexpressed by half of them. The CD45 RARO population contained higher percentage of cells that expressed KIRs, although it was statistically significant only for CD158e. The percentage of GzmB+ cells was similar to other subsets, but the intracellular level of this cytokine was lower. This could be due to a deficient production or a recent degranulation that has emptied the intracellular stores. CD45 RARO cells also expressed similar levels than CD45RA of another maturation marker the CD161/Killer cell lectin-like receptor subfamily B, member 1 (KLRB1) or the natural cytotoxicity receptor (NCR) NKP46 and slightly higher levels of the activating NKG2D receptor. However, they showed lower levels of the CD94 glycoprotein and, probably, the inhibitory NK receptor NKG2A. In summary, CD45 RARO cells are fully mature NK cells that mainly express NK receptors of mature cells.

Metabolic Characterization of CD45 RARO Population

Activated lymphocytes generally increase their size (Skak et al., 2008; Zarcone et al., 1987) and become highly metabolically active cells (Sanchez-Martinez et al., 2015; Sanchez-Martinez et al., 2014). The Ser/Thr kinase mTor probably links the metabolic shift and the cytoskeletal organization after NK cell activation (Marcais and Walzer, 2014). We observed a subset of NK cells from MM patients that was larger in size (FS) and with high granularity (SS) and corresponded to CD45 RARO cells (FIG. 7A). This suggested that they were activated cells that had a higher metabolic activity compared to the other NK subsets. Hence, we activated NK cells in vitro by incubating them with the Epstein Barr Virus (EBV) lymphoblastoid cell line PLH. To support NK cell survival we added low concentrations of two NK cell activating cytokines: IL-2 (100 U/ml) and IL-15 (5 ng/ml) (Anel et al., 2012). We incubated NK cells for up to 20 days to reflect long-term activation. In agreement with previous reports (Skak et al., 2008; Zarcone et al., 1987), 10-day activation induced an increase in size (FCS) and granularity (SSC) that was more relevant at day 20.

After 3 days of in vitro activation, NK cells started losing CD45RA. However, it was questionable if a real CD45 RARO population appeared or cells were losing CD45RA whereas gaining CD45RO. 10 days after initial activation, most cells are $CD45RA^-CD45RO^+$. However, at day 20 a CD45 RARO population appeared in the culture. This was not exclusive of the presence of accessory cells because long-term activation with cytokines produced a similar pattern. In summary, CD45 RARO NK cells also exist in vitro after long activation. Next, we evaluated in vitro activation of patient CD45 RARO population. Three days of cytokine-induced activation induced a strong rearrangement on the expression of CD45 isoforms and it was impossible to evaluate the faith of individual populations. These results additionally suggested that CD45 RARO cells could change their CD45 phenotype, at least in vitro.

We then assessed the expression of transferrin receptor protein 1 (TfR1 or CD71), which is required for iron delivery from transferrin to the cells. CD71 expression increases in active metabolic cells because iron is a cofactor for fundamental biochemical activities, such as oxygen transport, energy metabolism and DNA synthesis (Wang and Pantopoulos, 2011). In agreement with the superior metabolic activity suggested by high FS and SS of CD45 RARO cells, CD71 expression was higher in $CD45RO^+$ cells in both healthy controls and patients with hematological malignancies (FIG. 7B). Moreover, most of these cells also expressed the proliferation marker Ki-67 (FIG. 7C). In summary, CD45 RARO cells represent a NK subset of highly metabolic cells in proliferation.

CD69 expression increases after NK cell stimulation and is considered a bona fide marker of NK cell activation (Elpek et al., 2010), including ex vivo (Vey et al., 2012). Analysis of CD69 expression in the different CD45 populations in patients showed that CD45RO cells were mainly $CD69^+$ (FIG. 7D); but not vice versa, as most $CD69^+$ cells were not CD45RO. The very low amount of $CD45RO^+$ cells in healthy donors precluded any meaningful analysis of this population.

Figures 7D, 7E:
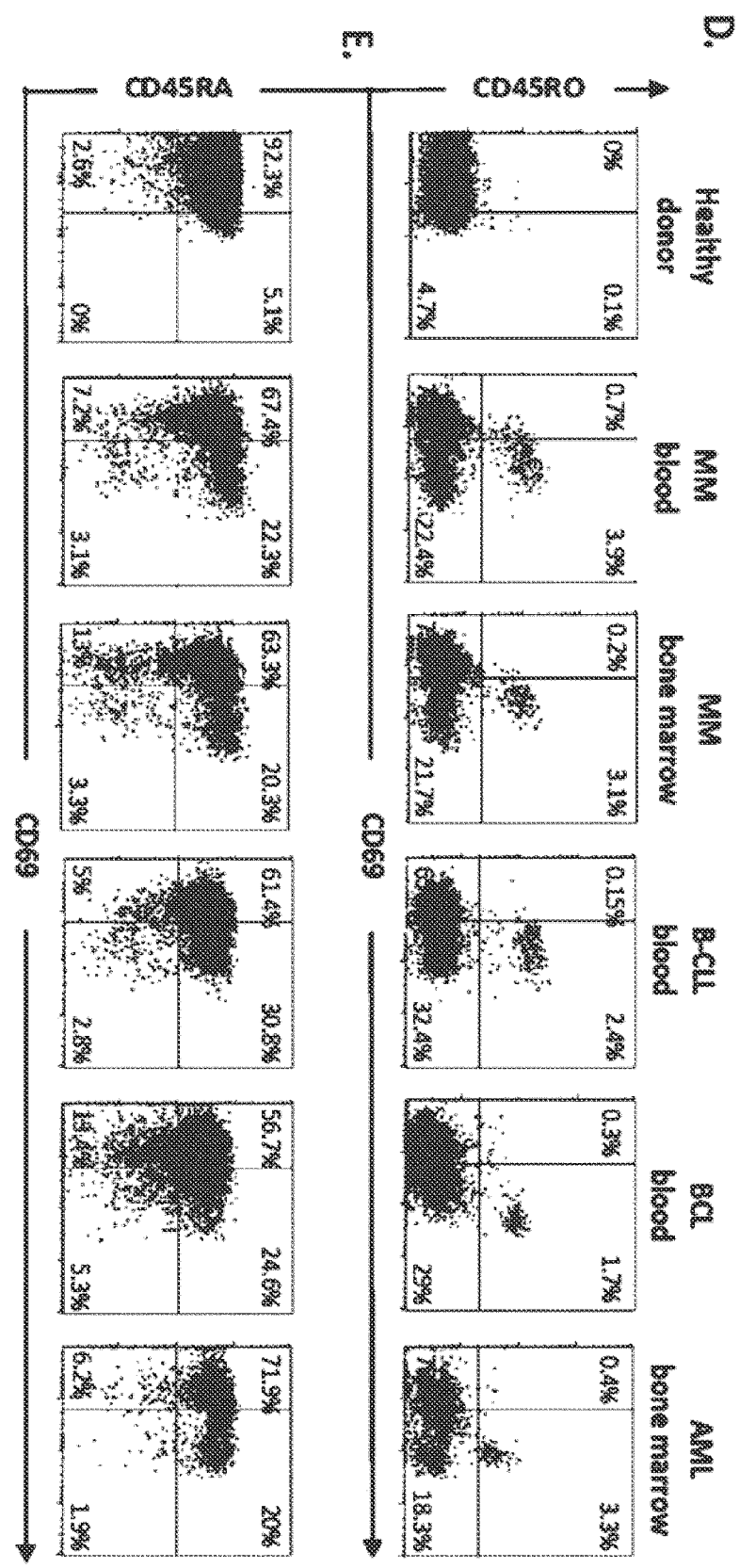

In healthy donors, $CD45RA^{dim}$ cells were mainly $CD69^-$ (FIG. 7E). $CD45RA^{dim}$ cells were significantly increased in patients and many were also $CD69^+$. However, reduction of CD45RA expression was not always associated with gain of CD69 expression. In fact, patients' samples were enriched particularly in $CD45RA^{dim}CD69^-$ and $CD45RA\ CD69^-$ and, to a lower extent, in $CD45RA^{dim}\ CD69^-$ cells. This finding suggests that loss of CD45RA and gain of CD69 expression identify two different physiological processes and that these two populations might have different functions.

Functional Characterization of CD45 RARO Population

To identify the function of the different NK cell subsets, first we assessed cell degranulation by ex vivo staining of PBMCs with anti-CD107a antibodies (FIG. 8A). In healthy donors, around 1% NK cells were $CD107a^+$. Most of these cells were CD45RA, with a small number of $CD45RO^-$ cells. Remarkably, most CD45 RARO and half of $CD45RA^{dim}RO$ cells were $CD107a^+$ (FIG. 8B).

NK cells from patients with hematological cancers showed a large increase in $CD107a^+$ cells (FIG. 8A), particularly among the $CD45RO^+$ subsets, which are specifically increased in these patients. Reduction of CD45RA expression was not associated with increased degranulation (FIG. 8B). Like in healthy donors, the CD45 RARO and, to a lower extent, $CD45RA^{dim}RO$ fractions contained mostly cells that had degranulated (FIG. 8B). The median CD107a-MFI of these two populations was largely increased compared to CD45RO⁻ populations. This was not exclusive of circulating NK cells, because similar results were obtained also for NK cells derived from bone marrow samples of patients with MM and AML (FIGS. 8B and 8C upper panels). In contrast, CD45 RARO cells showed low GzmB content. Our explanation is that CD45 RARO cells had recently degranulated in vivo.

CD45 RARO cells continued to show the higher degranulation rate after an in vitro analysis using K562 as target cells (FIG. 8C bottom panels), although other populations significantly increased degranulation. Interestingly, the different CD45 NK cell subsets did not change after the 4-hour in vitro cytotoxic assay. This and the in vitro activation results showed that expression of CD45RA and CD45RO is stable at short times but can change after long lasting activation.

Discussion:

Identification of new human NK cell populations is important for understanding their physiology and for improving their therapeutic use in the clinic. Here, we show that the identification of the different NK cell populations can also give valuable information about the host physiological status. Indeed, the presence of high numbers of CD45RA$^{dim}$ and CD45RO$^+$ cells in the mature compartment clearly identifies patients with hematological malignancies. We thus hypothesize that their detection could be used as a diagnostic tool of hematological cancers and also to assess the efficacy of antitumor treatments because these specific NK cell populations should decrease upon removal of the targeted tumor cells.

Leukemogenesis is enhanced when the host immune system is impaired (41, 42). Others and we have shown the requirement of fully functional NK cells to eradicate blood-borne tumors in several mouse models (43-48) and NK cell infiltration is associated with a good prognosis in several cancers (49-51). The use of alloreactive NK cells may represent a new cancer treatment, specifically for tumors of hematopoietic origin. Indeed, KIR-KIR ligand incompatibility in the graft-versus-host (GvH) direction, which is mainly based on NK cell alloreactivity, improves the outcome after unrelated cord blood stem cell transplantation (UCBT) in the clinic (52, 53). Moreover, NK cells: i) are not responsible of GvH disease (GvHD); ii) can be injected as "differentiated" cells and thus do not need to survive within the patient's body for a long time; iii) protect from opportunistic infections (52), probably through their immunoregulatory effects on B and T cells, macrophages and, more importantly, polymorphonuclear cells (54)). However, evaluation of NK cell activation in vivo is difficult because we lack effective methods for their analysis. CD69 expression has routinely been used (6, 17); however, our results show that CD69 expression does not imply degranulation and cytolytic activity, which is believed to be the most essential component of the NK cell anti-tumor activity (12). Conversely, our work indicates that CD45RO expression identifies degranulating NK cell subsets in patients with hematological malignancies. We believe that efficient antitumor treatments that involve also NK cell activity, such as monoclonal antibodies against tumor antigens, should also increase these NK cell populations.

Moreover, the most important unresolved problem before the standard use of allogeneic NK cells in the clinic is the engraftment of an adequate number of cells that show clinically efficient anti-tumor activity. For this purpose, it is crucial to identify the different NK cell populations and their cytolytic activity. Here, we show that the expression of CD45 isoforms should facilitate this task and that degranulation is enhanced in the CD45 RARO population. Hence, protocols increasing the CD45RO$^+$ subsets during autologous NK cell expansion should give better clinical results.

CD45 activity is regulated by dimerization and spontaneous CD45 homodimerization at the plasma membrane inhibits its activity (55). The size of CD45 extracellular domain is inversely proportional to the extent of CD45 dimerization and thus self-inhibition (55). Larger CD45 isoforms, such as CD45RA, dimerize less efficiently and, accordingly, they should better promote TCR signaling than smaller isoforms, such as CD45RO (19). However, CD45 activity also depends on its plasma membrane localization and thus on its extracellular domain (19, 56). At least in T cells, too high CD45 activity leads to dephosphorylation of the activating residues in Src kinases, whereas too low CD45 activity might leave phosphorylated the inhibitory residues. Therefore, it is important for efficient NK cell activation that CD45 activity remains within a specific window (26) and the amount of specific CD45 iso forms will regulate the final activity. We found that CD45 RARO NK cells show the maximal cytolytic activity, suggesting that expression of both CD45RA and CD45RO isoforms might give to NK cells the appropriate level of CD45 activity for efficient signaling to boost their cytolytic activity. This is in agreement with results in vivo in mice, where CD45 is required for full cytotoxic activity of NK cells (57). However, CD45 is not required for NK cell cytotoxicity in vitro (31-33). In agreement, we observed that in vitro also other NK cell subsets, which express different CD45 isoforms, show cytotoxic activity.

Moreover, expression of different CD45 isoforms changes the recognition of CD45 ligands. For example, the abundance and types of O-glycans on the different CD45 isoforms regulate the cell sensitivity to galectin-1 (58). Galectin-1, which is abundantly produced by tumor cells, blocks T cell-mediated cytotoxic responses (59) and induces apoptosis of thymocytes and T cells (58). It is possible that anti-tumor NK cells are selected based on their resistance to galectin-1 or to other ligands through expression of CD45RO. Indeed, as O-glycans bind mainly to CD45 extracellular domain, cells that express short CD45 isoforms, like CD45RO, will have relatively fewer O-glycans and thus will be more resistant to galectin-1.

Ex vivo we found very few NK cells that express CD45RO in peripheral blood samples from healthy donors. This is surprising, especially if CD45RO expression identifies memory NK cells, as it has been proposed (30). This finding suggests that the amount of memory NK cells might be extremely low in blood samples, or that CD45RO may not be a marker of memory NK cells. Alternatively, CD45RO expression in NK cells could have been specifically lost during ex vivo sample handling. We think that this is unlikely because NK cells express slightly higher levels of total CD45 than other lymphocyte types (FIG. 1). In fact, we found that CD45RO is mostly associated with effector NK cells; however, differently from what observed in most T cell populations, CD45RA down-regulation is not required for NK cell activation. This suggests that in NK cells the expression of different CD45 isoforms plays a different role than in T cells.

REFERENCES

Throughout this application, various references describe the state of the art to which this invention pertains. The disclosures of these references are hereby incorporated by reference into the present disclosure.

1. A. Velardi, Role of KIRs and KIR ligands in hematopoietic transplantation. *Curr Opin Immunol* 20, 581-587 (2008).
2. L. L. Lanier, Up on the tightrope: natural killer cell activation and inhibition. *Nat Immunol* 9, 495-502 (2008).
3. C. Baier, A. Fino, C. Sanchez, L. Farnault, P. Rihet, B. Kahn-Perles, R. T. Costello, Natural Killer Cells Modulation in Hematological Malignancies. *Frontiers in immunology* 4, 459 (2013).
4. M. Villalba, M. G. Rathore, N. Lopez-Royuela, E. Krzywinska, J. Garaude, N. Allende-Vega, From tumor cell metabolism to tumor immune escape. *Int J Biochem Cell Biol* 45, 106-113 (2013).
5. M. Villalba, N. Lopez-Royuela, E. Krzywinska, M. G. Rathore, R. A. Hipskind, H. Haouas, N. Allende-Vega, Chemical metabolic inhibitors for the treatment of blood-borne cancers. *Anti-cancer agents in medicinal chemistry* 14, 223-232 (2014).
6. N. Vey, J. H. Bourhis, N. Boissel, D. Bordessoule, T. Prebet, A. Charbonnier, A. Etienne, P. Andre, F. Romagne, D. Benson, H. Dombret, D. Olive, A phase 1 trial of the anti-inhibitory KIR mAb IPH2101 for AML in complete remission. Blood 120, 4317-4323 (2012).
7 D. H. McKenna, Jr., D. Sumstad, N. Bostrom, D. M. Kadidlo, S. Fautsch, S. McNearney, R. Dewaard, P. B. McGlave, D. J. Weisdorf, J. E. Wagner, J. McCullough, J. S. Miller, Good manufacturing practices production of natural killer cells for immunotherapy: a six-year single-institution experience. *Transfusion* 47, 520-528 (2007).
8. J. S. Miller, Y. Soignier, A. Panoskaltsis-Mortari, S. A. McNearney, G. H. Yun, S. K. Fautsch, D. McKenna, C. Le, T. E. Defor, L. J. Burns, P. J. Orchard, B. R. Blazar, J. E. Wagner, A. Slungaard, D. J. Weisdorf, I. J. Okazaki, P. B. McGlave, Successful adoptive transfer and in vivo expansion of human haploidentical NK cells in patients with cancer. Blood 105, 3051-3057 (2005).
9. L. Ruggeri, A. Mancusi, E. Burchielli, F. Aversa, M. F. Martelli, A. Velardi, Natural killer cell alloreactivity in allogeneic hematopoietic transplantation. *Curr Opin Oncol* 19, 142-147 (2007).
10. J. E. Rubnitz, H. Inaba, R. C. Ribeiro, S. Pounds, B. Rooney, T. Bell, C. H. Pui, W. Leung, NKAML: a pilot study to determine the safety and feasibility of haploidentical natural killer cell transplantation in childhood acute myeloid leukemia. *J Clin Oncol* 28, 955-959 (2010).
11. D. Sanchez-Martinez, E. Krzywinska, M. G. Rathore, A. Saumet, A. Cornillon, N. Lopez-Royuela, L. Martinez-Lostao, A. Ramirez-Labrada, Z. Y. Lu, J. F. Rossi, D. Fernandez-Orth, S. Escorza, A. Anel, C. H. Lecellier, J. Pardo, M. Villalba, All-trans retinoic acid (ATRA) induces miR-23a expression, decreases CTSC expression and granzyme B activity leading to impaired NK cell cytotoxicity. *Int J Biochem Cell Biol* 49, 42-52 (2014).
12. Y. T. Bryceson, S. C. Chiang, S. Darmanin, C. Fauriat, H. Schlums, J. Theorell, S. M. Wood, Molecular mechanisms of natural killer cell activation. *Journal of innate immunity* 3, 216-226 (2011).
13. C. I. Domaica, M. B. Fuertes, I. Uriarte, M. V. Girart, J. Sardanons, D. I. Comas, D. Di Giovanni, M. I. Gaillard, L. Bezrodnik, N. W. Zwirner, Human natural killer cell maturation defect supports in vivo CD56(bright) to CD56 (dim) lineage development. *PLoS One* 7, e51677 (2012).
14. L. Moretta, Dissecting CD56dim human NK cells. *Blood* 116, 3689-3691 (2010).
15. A. G. Freud, J. Yu, M. A. Caligiuri, Human natural killer cell development in secondary lymphoid tissues. *Seminars in immunology* 26, 132-137 (2014).
16. L. A. Fogel, M. M. Sun, T. L. Geurs, L. N. Carayannopoulos, A. R. French, Markers of nonselective and specific NK cell activation. *J Immunol* 190, 6269-6276 (2013).
17. K. G. Elpek, M. P. Rubinstein, A. Bellemare-Pelletier, A. W. Goldrath, S. J. Turley, Mature natural killer cells with phenotypic and functional alterations accumulate upon sustained stimulation with IL-15/IL-15Ralpha complexes. *Proc Natl Acad Sci USA* 107, 21647-21652 (2010).
18. R. Kaplan, B. Morse, K. Huebner, C. Croce, R. Howk, M. Ravera, G. Ricca, M. Jaye, J. Schlessinger, Cloning of three human tyrosine phosphatases reveals a multigene family of receptor-linked protein-tyrosine-phosphatases expressed in brain. *Proc Natl Acad Sci USA* 87, 7000-7004 (1990).
19. I. Rhee, A. Veillette, Protein tyrosine phosphatases in lymphocyte activation and autoimmunity. *Nat Immunol* 13, 439-447 (2012).
20. J. Irie-Sasaki, T. Sasaki, W. Matsumoto, A. Opaysky, M. Cheng, G. Welstead, E. Griffiths, C. Krawczyk, C. D. Richardson, K. Aitken, N. Iscove, G. Koretzky, P. Johnson, P. Liu, D. M. Rothstein, J. M. Penninger, CD45 is a JAK phosphatase and negatively regulates cytokine receptor signalling. *Nature* 409, 349-354 (2001).
21. K. Kishihara, J. Penninger, V. A. Wallace, T. M. Kundig, K. Kawai, A. Wakeham, E. Timms, K. Pfeffer, P. S. Ohashi, M. L. Thomas, et al., Normal B lymphocyte development but impaired T cell maturation in CD45-exon6 protein tyrosine phosphatase-deficient mice. *Cell* 74, 143-156 (1993).
22. K. F. Byth, L. A. Conroy, S. Howlett, A. J. Smith, J. May, D. R. Alexander, N. Holmes, CD45-null transgenic mice reveal a positive regulatory role for CD45 in early thymocyte development, in the selection of CD4+CD8+ thymocytes, and B cell maturation. *J Exp Med* 183, 1707-1718 (1996).
23. P. J. Mee, M. Turner, M. A. Basson, P. S. Costello, R. Zamoyska, V. L. Tybulewicz, Greatly reduced efficiency of both positive and negative selection of thymocytes in CD45 tyrosine phosphatase-deficient mice. *Eur J Immunol* 29, 2923-2933 (1999).
24. C. Kung, J. T. Pingel, M. Heikinheimo, T. Klemola, K. Varkila, L. I. Yoo, K. Vuopala, M. Poyhonen, M. Uhari, M. Rogers, S. H. Speck, T. Chatila, M. L. Thomas, Mutations in the tyrosine phosphatase CD45 gene in a child with severe combined immunodeficiency disease. *Nat Med* 6, 343-345 (2000).
25. E. Z. Tchilian, D. L. Wallace, R. S. Wells, D. R. Flower, G. Morgan, P. C. Beverley, A deletion in the gene encoding the CD45 antigen in a patient with SCID. *J Immunol* 166, 1308-1313 (2001).
26. M. L. Hermiston, J. Zikherman, J. W. Zhu, CD45, CD148, and Lyp/Pep: critical phosphatases regulating Src family kinase signaling networks in immune cells. *Immunol Rev* 228, 288-311 (2009).
27. H. S. Warren, L. J. Skipsey, Loss of activation-induced CD45RO with maintenance of CD45RA expression during prolonged culture of T cells and NK cells. *Immunology* 74, 78-85 (1991).
28. M. D. Roth, Interleukin 2 induces the expression of CD45RO and the memory phenotype by CD45RA+ peripheral blood lymphocytes. *J Exp Med* 179, 857-864 (1994).

29. K. W. Lynch, A. Weiss, A model system for activation-induced alternative splicing of CD45 pre-mRNA in T cells implicates protein kinase C and Ras. *Mol Cell Biol* 20, 70-80 (2000).
30. X. Fu, Y. Liu, L. Li, Q. Li, D. Qiao, H. Wang, S. Lao, Y. Fan, C. Wu, Human natural killer cells expressing the memory-associated marker CD45RO from tuberculous pleurisy respond more strongly and rapidly than CD45RO—natural killer cells following stimulation with interleukin-12. *Immunology* 134, 41-49 (2011).
31. N. D. Huntington, Y. Xu, S. L. Nutt, D. M. Tarlinton, A requirement for CD45 distinguishes Ly49D-mediated cytokine and chemokine production from killing in primary natural killer cells. *J Exp Med* 201, 1421-1433 (2005).
32. D. G. Hesslein, R. Takaki, M. L. Hermiston, A. Weiss, L. L. Lanier, Dysregulation of signaling pathways in CD45-deficient NK cells leads to differentially regulated cytotoxicity and cytokine production. *Proc Natl Acad Sci USA* 103, 7012-7017 (2006).
33. L. H. Mason, J. Willette-Brown, L. S. Taylor, D. W. McVicar, Regulation of Ly49D/DAP12 signal transduction by Src-family kinases and CD45. *J Immunol* 176, 6615-6623 (2006).
34. V. Beziat, B. Descours, C. Parizot, P. Debre, V. Vieillard, NK cell terminal differentiation: correlated stepwise decrease of NKG2A and acquisition of KIRs. *PLoS One* 5, e11966 (2010).
35. J. Clausen, B. Vergeiner, M. Enk, A. L. Petzer, G. Gastl, E. Gunsilius, Functional significance of the activation-associated receptors CD25 and CD69 on human NK-cells and NK-like T-cells. *Immunobiology* 207, 85-93 (2003).
36. K. Juelke, M. Killig, M. Luetke-Eversloh, E. Parente, J. Gruen, B. Morandi, G. Ferlazzo, A. Thiel, I. Schmitt-Knosalla, C. Romagnani, CD62L expression identifies a unique subset of polyfunctional CD56dim NK cells. *Blood* 116, 1299-1307 (2010).
37. S. Lopez-Verges, J. M. Milush, S. Pandey, V. A. York, J. Arakawa-Hoyt, H. Pircher, P. J. Norris, D. F. Nixon, L. L. Lanier, CD57 defines a functionally distinct population of mature NK cells in the human CD56dimCD16+NK-cell subset. *Blood* 116, 3865-3874 (2010).
38. M. Della Chiesa, L. Muccio, A. Moretta, CMV induces rapid NK cell maturation in HSCT recipients. *Immunology letters* 155, 11-13 (2013).
39. J. Siewiera, H. El Costa, J. Tabiasco, A. Berrebi, G. Cartron, P. Le Bouteiller, N. Jabrane-Ferrat, Human cytomegalovirus infection elicits new decidual natural killer cell effector functions. *PLoS pathogens* 9, e1003257 (2013).
40. J. Wang, K. Pantopoulos, Regulation of cellular iron metabolism. *Biochem J* 434, 365-381 (2011).
41. J. Garaude, S. Kaminski, S. Charni, J. I. Aguilo, C. Jacquet, M. Plays, J. Hernandez, F. Rodriguez, R. A. Hipskind, A. And, M. Villalba, Impaired anti-leukemic immune response in PKCtheta-deficient mice. *Mol Immunol* 45, 3463-3469 (2008).
42. S. Kaminski, O. Adjali, C. Jacquet, J. Garaude, A. Keriel, A. Lassaux, R. Hipskind, M. Sitbon, N. Taylor, M. Villalba, The protooncogene Vav1 regulates murine leukemia virus-induced T-cell leukemogenesis. *Oncoimmunology* 1, 600-608 (2012).
43. K. Kane, H. G. Ljunggren, G. Piontek, R. Kiessling, Selective rejection of H-2-deficient lymphoma variants suggests alternative immune defence strategy. *Nature* 319, 675-678 (1986).
44. M. F. van den Broek, D. Kagi, R. M. Zinkernagel, H. Hengartner, Perforin dependence of natural killer cell-mediated tumor control in vivo. *Eur J Immunol* 25, 3514-3516 (1995).
45. J. Pardo, S. Balkow, A. Anel, M. M. Simon, Granzymes are essential for natural killer cell-mediated and perf-facilitated tumor control. *Eur J lmmunol* 32, 2881-2887 (2002).
46. J. I. Aguilo, J. Garaude, J. Pardo, M. Villalba, A. Anel, Protein kinase C-theta is required for NK cell activation and in vivo control of tumor progression. *J lmmunol* 182, 1972-1981 (2009).
47. S. Charni, J. I. Aguilo, J. Garaude, G. de Bettignies, C. Jacquet, R. A. Hipskind, D. Singer, A. Anel, M. Villalba, ERK5 Knockdown generates mouse leukemia cells with low MHC class i levels that activate NK cells and block tumorigenesis. *J lmmunol* 182, 3398-3405 (2009).
48. S. Charni, G. de Bettignies, M. G. Rathore, J. I. Aguilo, P. J. van den Elsen, D. Haouzi, R. A. Hipskind, J. A. Enriquez, M. Sanchez-Beato, J. Pardo, A. Anel, M. Villalba, Oxidative phosphorylation induces de novo expression of the MHC class I in tumor cells through the ERK5 pathway. *J lmmunol* 185, 3498-3503 (2010).
49. L. Senovilla, E. Vacchelli, J. Galon, S. Adjemian, A. Eggermont, W. H. Fridman, C. Sautes-Fridman, Y. Ma, E. Tartour, L. Zitvogel, G. Kroemer, L. Galluzzi, Trial watch: Prognostic and predictive value of the immune infiltrate in cancer. *Oncoimmunology* 1, 1323-1343 (2012).
50. E. Mamessier, L. C. Pradel, M. L. Thibult, C. Drevet, A. Zouine, J. Jacquemier, G. Houvenaeghel, F. Bertucci, D. Birnbaum, D. Olive, Peripheral blood NK cells from breast cancer patients are tumor-induced composite subsets. *J lmmunol* 190, 2424-2436 (2013).
51. E. Mamessier, F. Bertucci, R. Sabatier, D. Birnbaum, D. Olive, "Stealth" tumors: Breast cancer cells shun NK-cells anti-tumor immunity. *Oncoimmunology* 1, 366-368 (2012).
52. R. Willemze, C. A. Rodrigues, M. Labopin, G. Sanz, G. Michel, G. Socie, B. Rio, A. Sirvent, M. Renaud, L. Madero, M. Mohty, C. Ferra, F. Gamier, P. Loiseau, J. Garcia, L. Lecchi, G. Kogler, Y. Beguin, C. Navarrete, T. Devos, I. Ionescu, K. Boudjedir, A. L. Herr, E. Gluckman, V. Rocha, KIR-ligand incompatibility in the graft-versus-host direction improves outcomes after umbilical cord blood transplantation for acute leukemia. *Leukemia* 23, 492-500 (2009).
53. M. Stern, L. Ruggeri, A. Mancusi, M. E. Bernardo, C. de Angelis, C. Bucher, F. Locatelli, F. Aversa, A. Velardi, Survival after T cell-depleted haploidentical stem cell transplantation is improved using the mother as donor. *Blood* 112, 2990-2995 (2008).
54. N. Bhatnagar, H. S. Hong, J. K. Krishnaswamy, A. Haghikia, G. M. Behrens, R. E. Schmidt, R. Jacobs, Cytokine-activated NK cells inhibit PMN apoptosis and preserve their functional capacity. *Blood* 116, 1308-1316 (2010).
55. Z. Xu, A. Weiss, Negative regulation of CD45 by differential homodimerization of the alternatively spliced isoforms. *Nat Immunol* 3, 764-771 (2002).
56. T. Mustelin, T. Vang, N. Bottini, Protein tyrosine phosphatases and the immune response. *Nat Rev Immunol* 5, 43-57 (2005).
57. D. G. Hesslein, E. H. Palacios, J. C. Sun, J. N. Beilke, S. R. Watson, A. Weiss, L. L. Lanier, Differential requirements for CD45 in NK-cell function reveal distinct roles for Syk-family kinases. *Blood* 117, 3087-3095 (2011).

58. L. A. Earl, S. Bi, L. G. Baum, N- and O-glycans modulate galectin-1 binding, CD45 signaling, and T cell death. *J Biol Chem* 285, 2232-2244 (2010).

59. K. Ito, K. Stannard, E. Gabutero, A. M. Clark, S. Y. Neo, S. Onturk, H. Blanchard, S. J. Ralph, Galectin-1 as a potent target for cancer therapy: role in the tumor microenvironment. *Cancer metastasis reviews* 31, 763-778 (2012).

The invention claimed is:

1. A method for diagnosing and for treating a haematological cancer in a patient comprising:
   i) obtaining a blood sample or a bone marrow sample from a patient,
   ii) detecting the presence of CD45 RARO NK cells in the sample obtained from the patient using of a set of binding partners that are suitable for distinguishing NK cells from other cells and a set of binding partners comprising at least one differential binding partner specific for CD45RA and at least one differential binding partner specific for CD45RO,
   iii) concluding that the patient suffers from a haematological cancer when the presence of CD45 RARO NK cells is detected in the sample, and
   iv) treating the patient suffering from a haematological cancer with a chemotherapeutic agent, a targeted cancer therapy, an immunotherapeutic agent or a radiotherapeutic agent.

2. The method of claim 1 wherein the haematological cancer is selected from the group consisting of leukemia, lymphoma and myeloma.

3. The method of claim 2 wherein the haematological cancer is a mature (peripheral) B-cell neoplasm.

4. The method of claim 3 wherein the haematological cancer is selected from the group consisting of B-cell chronic lymphocytic leukemia/small lymphocytic lymphoma; B-cell prolymphocytic leukemia; Lymphoplasmacytic lymphoma; Marginal zone lymphoma, such as Splenic marginal zone B-cell lymphoma (+/−villous lymphocytes), Nodal marginal zone lymphoma (+/−monocytoid B-cells), and Extranodal marginal zone B-cell lymphoma of mucosa-associated lymphoid tissue (MALT) type; Hairy cell leukemia; Plasma cell myeloma/plasmacytoma; Follicular lymphoma, follicle center; Mantle cell lymphoma; Diffuse large cell B-cell lymphoma (including Mediastinal large B-cell lymphoma, Intravascular large B-cell lymphoma, and Primary effusion lymphoma); and Burkitt's lymphoma/Burkitt's cell leukemia.

5. The method of claim 2 wherein the haematological cancer is selected from the group consisting of multiple myeloma (MM) and non-Hodgkin's lymphoma (NHL), mantle cell lymphoma (MCL), follicular lymphoma, Waldenstrom's macroglobulinemia (WM) or B-cell lymphoma and diffuse large B-cell lymphoma (DLBCL).

6. The method of claim 5 wherein the haematological cancer is selected from the group consisting of B-cell neoplasms, diffuse large B-cell lymphoma, T/NK cell neoplasms, anaplastic large cell lymphoma, peripheral T-cell lymphomas, precursor B-lymphoblastic leukemia/lymphoma, precursor T-lymphoblastic leukemia/lymphoma, Burkitt's lymphoma, Adult T-cell lymphoma/leukemia (HTLV1+), primary CNS lymphoma, mantle cell lymphoma, polymorphic post-transplantation lymphoproliferative disorder (PTLD), AIDS-related lymphoma, true histiocytic lymphoma, and blastic NK-cell lymphoma.

7. The method of claim 2 wherein the leukemia is selected from the group consisting of acute lymphocytic leukemia (ALL), acute myeloid leukemia (AML), chronic lymphocytic leukemia (CLL), and small lymphocytic lymphoma (SLL).

8. The method of claim 1 which further comprises the steps of detecting the presence of at least one phenotypic marker on said CD45 RARO NK cells wherein:
   the presence of at least one phenotypic marker selected from the group consisting of CD5, CD10, CD19, CD20, CD22, CD23, CD24, CD79a, CD103, Pax-5, kappa, lambda, CD200, cytoplasmic kappa, or cytoplasmic lambda indicates that the hematological cancer originates from a B cell;
   the presence of at least one phenotypic marker selected from the group consisting of CD1, CD2, CD3, CD4, CD5, CD7, CD8, TCR α-β, TCR γ-δ, and CD3 indicates that the hematological cancer originates from a T cell; or
   the presence of at least one phenotypic marker selected from the group consisting of CD11b, CD13, CD14 (Mo2), CD14 (MY4), CD15, CD33, CD41, CD61 CD64, CD117, CD235a and myeloperoxidase indicates that the haematological cancer originates from a myeloid cell.

9. A method for monitoring the efficiency of a treatment in a patient suffering from an haematological cancer comprising:
   i) treating a patient suffering from a haematological cancer with a chemotherapeutic agent, a targeted cancer therapy, an immunotherapeutic agent or a radiotherapeutic agent,
   ii) obtaining a blood sample or a bone marrow sample from said patient,
   iii) detecting the presence of CD45 RARO NK cells in the sample from the patient using of a set of binding partners that are suitable for distinguishing NK cells from other cells and a set of binding partners comprising at least one differential binding partner specific for CD45RA and at least one differential binding partner specific for CD45RO, and
   iv) concluding that the treatment of the patient is efficient when the presence of CD45 RARO NK cells is not detected in the blood sample.

* * * * *